(12) United States Patent
Savage

(10) Patent No.: US 9,533,063 B1
(45) Date of Patent: Jan. 3, 2017

(54) AEROSOLS INCORPORATING CERAGENIN COMPOUNDS AND METHODS OF USE THEREOF

(71) Applicant: Paul B. Savage, Mapleton, UT (US)

(72) Inventor: Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 361 days.

(21) Appl. No.: 13/783,007

(22) Filed: Mar. 1, 2013

Related U.S. Application Data

(60) Provisional application No. 61/605,642, filed on Mar. 1, 2012.

(51) Int. Cl.
  *A61L 2/18* (2006.01)
  *A61L 2/22* (2006.01)

(52) U.S. Cl.
  CPC ........................................ *A61L 2/22* (2013.01)

(58) Field of Classification Search
  CPC .......................................................... A61L 2/22
  USPC ............................................................ 422/28
  See application file for complete search history.

(56) References Cited

U.S. PATENT DOCUMENTS

| | | |
|---|---|---|
| 4,661,341 A | 4/1987 | Benedict et al. |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,721,359 A | 2/1998 | Dunn et al. |
| 6,117,332 A | 9/2000 | Hatch et al. |
| 6,228,393 B1 | 5/2001 | DiCosmo et al. |
| 6,350,738 B1 | 2/2002 | Savage |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.

(Continued)

*Primary Examiner* — Kevin Joyner
(74) *Attorney, Agent, or Firm* — Workman Nydegger

(57) ABSTRACT

Aerosols that include ceragenin compounds (i.e., ceragenin-containing aerosols), methods for delivering such aerosols, and devices for delivering such aerosols. Ceragenins can be used to kill a broad range of microbes (e.g., bacteria, viruses, fungi, bacterial spores, fungal spores, and the like), yet they are thought to be completely non-toxic to humans and other higher eukaryotes. Aerosols can penetrate into the nooks and crannies of a space and kill microbes that may lurk in a space. In addition, ceragenins have a extended mode of action, which allows them to continue killing microbes in a space for an extended period of time.

26 Claims, 15 Drawing Sheets

(56) References Cited

U.S. PATENT DOCUMENTS

| | | |
|---|---|---|
| 6,486,148 B2 | 11/2002 | Savage et al. |
| 6,562,318 B1 | 5/2003 | Filler |
| 6,673,771 B1 | 1/2004 | Greene et al. |
| 6,767,904 B2 | 7/2004 | Savage et al. |
| 6,803,066 B2 | 10/2004 | Traeder |
| 6,872,303 B2 | 3/2005 | Knapp et al. |
| 6,939,376 B2 | 9/2005 | Shulze et al. |
| 7,282,214 B2 | 10/2007 | Willcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 | 7/2010 | Savage et al. |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff |
| 8,691,252 B2 | 4/2014 | Savage |
| 8,784,857 B2 | 7/2014 | Savage |
| 8,787,857 B2 | 7/2014 | Ezaki |
| 2002/0091278 A1 | 7/2002 | Savage et al. |
| 2003/0099717 A1* | 5/2003 | Cabrera ............ 424/616 |
| 2004/0009227 A1 | 1/2004 | Yao |
| 2004/0058974 A1 | 3/2004 | Courtney et al. |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0106393 A1 | 5/2007 | Miles et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0174035 A1 | 7/2008 | Winterton |
| 2008/0188819 A1 | 8/2008 | Kloke et al. |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0324517 A1 | 12/2009 | Kline |
| 2010/0092398 A1* | 4/2010 | Reynolds ............ A61K 36/61 424/43 |
| 2010/0226884 A1 | 9/2010 | Chang et al. |
| 2010/0330086 A1 | 12/2010 | Savage et al. |
| 2011/0091376 A1 | 4/2011 | Savage |
| 2011/0123624 A1 | 5/2011 | Zasloff |
| 2012/0088733 A1 | 4/2012 | Kim et al. |
| 2012/0107382 A1 | 5/2012 | Savage |
| 2013/0022651 A1 | 1/2013 | Savage |
| 2013/0053507 A1 | 2/2013 | Savage |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0243842 A1 | 9/2013 | Genberg et al. |
| 2013/0245760 A1 | 9/2013 | Savage et al. |
| 2013/0280312 A1* | 10/2013 | De Szalay ............ 424/408 |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0271761 A1 | 9/2014 | Savage et al. |
| 2014/0274913 A1 | 9/2014 | Savage et al. |
| 2014/0315873 A1 | 10/2014 | Beus et al. |
| 2014/0363780 A1 | 12/2014 | Vazquez et al. |
| 2014/0369941 A1 | 12/2014 | Vazquez et al. |
| 2015/0140063 A1 | 5/2015 | Savage |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |

FOREIGN PATENT DOCUMENTS

| | | |
|---|---|---|
| EP | 0341951 | 11/1989 |
| EP | 1208844 | 5/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | 95-24415 | 9/1995 |
| WO | WO 9944616 | 9/1999 |
| WO | WO 0042058 | 7/2000 |
| WO | WO 0214342 | 2/2002 |
| WO | WO02067979 | 9/2002 |
| WO | 03-015757 | 2/2003 |
| WO | WO 03090799 | 11/2003 |
| WO | WO2004082588 | 9/2004 |
| WO | WO 2004112852 | 12/2004 |
| WO | 2007-089903 | 8/2007 |
| WO | 2007-089906 | 8/2007 |
| WO | 2007-089907 | 8/2007 |
| WO | WO 2007134176 | 11/2007 |
| WO | WO 2008038965 | 4/2008 |
| WO | 2009-079066 | 6/2009 |
| WO | WO2010006192 | 1/2010 |
| WO | 2010-036427 | 4/2010 |
| WO | WO 2010062562 | 6/2010 |
| WO | WO2011066260 | 6/2011 |
| WO | 2011-109704 | 9/2011 |
| WO | 2012-061651 | 5/2012 |
| WO | WO 2013029055 | 2/2013 |
| WO | WO 2013029059 | 2/2013 |
| WO | WO2013/109236 | 7/2013 |

OTHER PUBLICATIONS

Britton et al, "Imaging bacterial infection with 99mTc-ciprofloxacin (Infection)", Journal of Clinical Pathology, vol. 55, pp. 817-823, Apr. 6, 2015.

Suzuki et al., "Molecular Genetics of Plant Sterol Backbone Synthesis", 2007; Lipids; 42: 47-54.

Van Den Bogaard et al., "Antibiotic Usage in Animals: Impact on Bacterial Resistance and Public Health"; 1999; Drugs; 58 (4): 589-607.

U.S. Appl. No. 13/615,244, filed Sep. 13, 2012, Office Action dated Jan. 16, 2015.

U.S. Appl. No. 14/257,776, filed Apr. 21, 2014, Restriction Requirement dated Jan. 22, 2015.

U.S. Appl. No. 14/364,283, filed Jul. 29, 2014, Office Action dated Feb. 11, 2015.

U.S. Appl. No. 14/339,342, filed Jul. 23, 2014, Office Action dated Mar. 5, 2015.

U.S. Appl. No. 13/554,930, filed Jul. 20, 2012, Final Office Action dated Mar. 16, 2015.

U.S. Appl. No. 13/000,010, filed Dec. 17, 2010, Office Action dated Apr. 14, 2015.

U.S. Appl. No. 14/257,776, filed Apr. 21, 2014, Office Action dated Apr. 16, 2015.

U.S. Appl. No. 14/288,126, filed May 27, 2014, Savage, et al.

U.S. Appl. No. 14/339,342, filed Jul. 23, 2014, Vazquez, et al.

U.S. Appl. No. 14/341,304, filed Jul. 25, 2014, Savage, et al.

U.S. Appl. No. 14/364,283, filed Jul. 29, 2014, Vazquez, et al.

U.S. Appl. No. 14/515,858, filed Oct. 16, 2014, Savage, et al.

U.S. Appl. No. 14/398,094, filed Oct. 30, 2014, Savage, et al.

Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.

(56) References Cited

OTHER PUBLICATIONS

Savage, et al., "Antibacterial Activities of Thin Films Containing Ceragenins", Microbial Surfaces: Structure, Interactions and Reactivity, ACS, May 30, 2008, pp. 65-78.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
International Search Report for PCT Application No. PCT/US2012/047750, Mailed Date: Oct. 5, 2012, Filed Date: Sep. 27, 2012, 3 pages.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Paul B. Savage, et al: "Antibacterial Properties of cationic steroid antibiotics", FEMS Microbiology Letters, vol. 217, Nov. 2002, pp. 1-7.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
Li Chunhong, et al., "Antimicrobial Activities of Amine—and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
International Search Report for PCT Application No. PCT/US2009/047485 dated Feb. 17, 2010.
International Search Report for PCT Application No. PCT/US2013/038090, Mailed Date: Jul. 24, 2013.
Steeneveld, et al., "Cow-specific treatment of clinical mastitis: an economic approach", Journal of Dairy Science vol. 94, Jan. 2011, pp. 174-188.
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/o10062704/suppl file/o10062704 sl.pdf.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
International Search Report for PCT Application No. PCT/US2011/059225 dated Jan. 31, 2012.
International Search Report for PCT Application No. PCT/US2012/055248 dated Feb. 14, 2013.
International Search Report for PCT Application No. PCT/US2012/047750 dated Oct. 5, 2012.
International Search Report for PCT Application No. PCT/US2012/055244 dated Dec. 5, 2012.
U.S. Appl. No. 13/554,957, Aug. 1, 2014, Notice of Allowance.
U.S. Appl. No. 13/594,612, May 15, 2014, Office Action.
U.S. Appl. No. 13/554,930, Jul. 11, 2014, Office Action.
U.S. Appl. No. 13/783,131, Oct. 23, 2014, Office Action.
U.S. Appl. No. 13/000,010, Dec. 4, 2012, Restriction Requirement.
U.S. Appl. No. 13/288,902, Jun. 21, 2012, Restriction Requirement.
U.S. Appl. No. 13/288,902, Nov. 7, 2012, Office Action.
U.S. Appl. No. 13/288,902, Aug. 9, 2013, Notice of Allowance.
U.S. Appl. No. 13/288,892, Dec. 10, 2012, Restriction Requirement.
U.S. Appl. No. 13/288,892, May 9, 2013, Office Action.
U.S. Appl. No. 13/288,892, Nov. 29, 2013, Notice of Allowance.
U.S. Appl. No. 14/056,122, Sep. 3, 2014, Office Action.
P. B. Savage et al.: "Thin Films Containing Ceragenins Prevent Biofilm Formation on Endotracheal Tubes." 9th International Federation of Infection Control Congress. Oct. 14, 2008. pp. 1-1.
Xin-Zhong Lai et al: "Ceragenins: Cholic Acid-Based Mimics of Antimicrobial peptides", Account of Chemical Research vol. 41, No. 10, Oct. 21, 2008, pp. 1233-1240.
K.D. Sinclair et al: "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Michael D Howell et al: "Ceragenins: A 1-18, Class of Antiviral Compounds to Treat Orthopox Infections", Journal of Investigative Dermatology, vol. 129, No. 11, Jun. 11, 2009 (Jun. 11, 2009), pp. 2668-2675.
K. Leszczynska et al: "Potential of ceragenin CSA-13 and its mixture with pluronic F-127 as treatment of topical bacterial infections", Journal of Applied Microbiology, vol. 110, No. 1, Oct. 21, 2010 (Oct. 21, 2010), pp. 229-238.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Alhanout K et al: "Squalamine as an example of a new potent antimicrobial agents class: a critical review.", Current Medicinal Chemistry 2010, vol. 17, No. 32, 2010, pp. 3909-3917.
U.S. Appl. No. 13/615,324, Jan. 30, 2014, Office Action.
U.S. Appl. No. 13/594,608, Jan. 30, 2014, Office Action.
U.S. Appl. No. 13/554,957, Apr. 1, 2014, Office Action.
U.S. Appl. No. 14/694,028, filed Apr. 23, 2015, Beus et al.
U.S. Appl. No. 14/750,928, filed Jun. 25, 2015, Genberg et al.
U.S. Appl. No. 14/830,356, filed Aug. 19, 2015, Savage.
U.S. Appl. No. 14/842,582, filed Nov. 1, 2015, Genberg et al.
U.S. Appl. No. 14/848,819, filed Nov. 9, 2015, Genberg et al.
U.S. Appl. No. 14/866,213, filed Sep. 25, 2015, Savage.
U.S. Appl. No. 14/873,013, filed Oct. 1, 2012, Savage et al.
U.S. Appl. No. 14/875,953, filed Oct. 6, 2015, Savage.
U.S. Appl. No. 14/926,738, filed Oct. 29, 2015, Vazquez et al.
Alafort et al., "Lys and Arg in UBI: A specific site for a stable Tc-99m complex?", Nuclear Medicine and Biology 30 (2003) 605-615.
Berge et al., "Pharmaceutical Salts", Journal of Pharmaceutical Sciences, Jan. 1977, vol. 66, No. 1, pp. 1-19.
Brown, "Bioisosteres in Medicinal Chemistry, First Edition", ediated by Nathan Brown, 2012, Ch. 2 Classical Bioisosteres, pp. 1-52.
Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.
Clara et al., "Preclinical evaluation of magainin-A as a contraceptive antimicrobial agent", Fertility and Sterility 81 (5), pp. 1357-1365, 2004.
Fichna et al., "Synthesis of Target-Specific Radiolabeled Peptides for Diagnostic Imaging", Bioconjugate Chem., 2003, 14, 3-17, American Chemical Society.

(56) References Cited

OTHER PUBLICATIONS

International Search Report for PCT Application No. PCT/US2014/034986 dated Aug. 28, 2014.
International Search Report for PCT Application No. PCT/US2013/065510, dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2015/046412 dated Dec. 1, 2015.
International Search Report for PCT Application No. PCT/US2015/054434 dated Dec. 23, 2015.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Lankinen et al., "Ga-Dota-Peptide Targeting VAP-1 for In Vivo Evaluation of Inflammatory and Infetious Bone Conditions", 52nd Annual Meeting of the Orthopaedic Research Society.
Li et al., "Incremental conversin of Outer-Membrane Permeabilizers into Potent Antibiotics for Gram-Negative Bacteria", J. Am. Chem. Soc. 1999, 121, 9310-940.
Lowe et al., "Effect of Hydrophobicity of a Drug on its Release from Hydrogels with Different Topological Structures" Journal of Polymer Science (1999) 73: 1031-1039 (9 pages).
Massoud et al., "Molecular imaging in living subjects: seeing fundamental biological processes in a new light", Genes & Development 17: 545-580 2003, Cold Spring Harbor Laboratory Press.
Muñoz-Juárez et al., "Wide-Lumen Stapled Anastomosis vs. Conventional End-to-End Anastomosis in the Treatment of Crohn's Disease", Dis Colon Rectum 2001 ; 44: No. 1, 20-26).
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Welling et al., "Radiochemical and biological characteristics of 99m-Tc-UBI 29-41 for imaging of bacterial infections", Nuclear Medicine and Biology 29 (2002) 413-422.
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
Zanger et al., "Structure-Activity Relationship and Drug Design", Remington's Pharmaceutical Sciences, Chapter 27, 16th Edition, 1980, pp. 420-425.

\* cited by examiner

CSA-37

CSA-41

CSA-42

CSA-43

CSA-44

CSA-45

CSA-47

CSA-49

CSA-50

CSA-51

CSA-1

CSA-2

CSA-3

CSA-4

CSA-5

CSA-6

CSA-7

CSA-8

CSA-10

CSA-11

CSA-105

CSA-106

CSA-107

CSA-109

CSA-110

CSA-112

CSA-113

CSA-118

CSA-119

CSA-120

CSA-121

CSA-121a

CSA-122

CSA-123

CSA-124

CSA-130    CSA-131

CSA-132

AEROSOLS INCORPORATING CERAGENIN COMPOUNDS AND METHODS OF USE THEREOF

CROSS-REFERENCE TO RELATED APPLICATION

This application claims the benefit of U.S. Provisional Patent Application No. 61/605,642, filed Mar. 1, 2012, the disclosure of which is incorporated herein in its entirety.

BACKGROUND OF THE INVENTION

Eliminating and diminishing harmful microbes (e.g., bacteria, fungi, and viruses and bacterial and fungal spores) is a major concern. In a household, hospital, or food preparation facility setting, for example, harmful microbes may reside on a variety of surfaces and in the air. Such microbes may cause illness, irritation, or exacerbate allergies. Various products are available to reduce or eliminate such microbes.

In the environment, products such as liquid or spray disinfectants may be used to reduce or eliminate harmful microbes. Liquid disinfectants are typically mixed with water and used to clean surfaces such as bathroom/kitchen counters, kitchen sink areas, food preparation areas, walls and baseboards, and the like. These liquid disinfectants and methods of surface cleaning may be effective in reducing microbial contamination. For example, liquid disinfectants can be effective in reducing microbial contamination by simple cleaning action or through the use of anti-microbial agents. However, such compositions are only effective in the areas directly contacted by the composition. In addition, many anti-microbial compounds are associated with the development of resistance, particularly among bacteria.

When harmful microbes cause infection in a body (e.g., a human or animal body), antibiotics, antifungals, antivirals, and the like are generally prescribed. For example, antibiotics such as penicillin and penicillin derivatives may be used to treat a wide variety of bacterial infections. However, it is often necessary to administer antibiotics, antifungals, antivirals, and the like systemically even though the site of infection may be localized. In addition, as with anti-microbials used for environmental decontamination, many antibiotics, antifungals, antivirals, and the like are associated with the development of resistance.

BRIEF SUMMARY

Disclosed herein are aerosols that include ceragenin compounds (i.e., ceragenin-containing aerosols), methods for delivering such aerosols, and devices for delivering such aerosols. Ceragenins (or cationic steroidal antimicrobial (CSA) compounds) can be used to kill a broad range of microbes (e.g., bacteria, viruses, fungi, bacterial spores, fungal spores, and the like), yet they are non-toxic to humans and other higher eukaryotes. Surprisingly, it has been found that ceragenins dispersed in aerosols are selective against harmful bacteria as compared to normal flora. The effectiveness at lower concentrations facilitates killing harmful bacteria in remote or hard to reach spaces or within biological organisms where lower concentrations are preferred. Aerosols of or in devices that provide relatively low concentrations of the compound are preferred (e.g., in pharmaceutical applications).

Forming small ceragenin particles (e.g., colloidal particles) allows the particles to stay suspended long enough to be carried throughout a room or other space before condensing on a surface. This feature, coupled with the selective killing of harmful bacteria, can be largely responsible for effective killing of harmful bacteria in nooks and crannies of a space and kill microbes that may lurk there. In one embodiment, ceragenins in aerosol form are at least 5 fold, 15, fold, 25 fold, or even 50 fold more potent at killing harmful microbes as compared to normal flora.

Another benefit of some compositions of the present invention is an extended mode of action, which allows them to continue killing microbes in a space for an extended period of time. This can be accomplished, for example, by selecting a pH for the composition that stabilizes the ceragenin for a desired period of time.

Aerosols described herein can include gaseous suspensions of ceragenin compounds. The ceragenin compounds may be included in the gaseous suspension in the form of very fine, e.g., micronized liquid droplets and/or micronized ceragenin particles. Such aerosols may fill a space (e.g., a room or conduit) such that the ceragenins can come into contact with and deposit onto microbe-exposed surfaces in the space. Ceragenins deposited on microbe-exposed surfaces can kill microbes that are on the surface(s) at the time of deposition. Likewise, ceragenins can also kill microbes that may land on the surface(s) until the ceragenins are either degraded or removed from the surface(s).

In one embodiment, a method for delivering a ceragenin to a space is disclosed. The method includes: (1) dispersing an aerosol of a ceragenin composition in a space, wherein the space includes one or more microbe-exposed surfaces; (2) contacting the one or more microbe-exposed surfaces in the space with the aerosol; and (3) depositing the ceragenin composition on the one or more microbe-exposed surfaces contacted by the aerosol.

In another embodiment, a device for delivering a ceragenin-containing aerosol is described. The device includes a ceragenin source and a means for dispersing the ceragenin in an aerosol form. Suitable examples of means for dispersing the ceragenin in an aerosol form include, but are not limited to, compressed gas canisters, thermal foggers, spinning disc foggers, nebulizers, and the like.

The ceragenin-containing aerosols described herein may be distributed in a space by passive diffusion, or they may be distributed by forced air currents. In either case, aerosols can be distributed in the space in much the same way that microbes are distributed, i.e., on air currents. Therefore, the ceragenins can penetrate into all of the nooks and crannies in the space where the microbes may lurk.

In addition, ceragenins can be largely inert in a desiccated state and become activated in the presence of water. Similarly, many bacteria, fungi, and their spores also become inactive in the absence of water and are activated in the presence of water. In one embodiment, ceragenin-containing aerosol may be distributed as an aqueous-based dispersion (e.g., a fog). As the aerosol settles onto surfaces in the space, the aerosol may hydrate dried microbes on the surface, which can allow the aerosol to "activate" and kill microbes in one step.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawing. It is appreciated that this drawing depicts only illustrated embodiments of the invention and is therefore not to be considered limiting of its scope. The invention will be described and explained with additional specificity and detail through the use of the accompanying drawing in which.

DETAILED DESCRIPTION

I. Introduction

Ceragenin compounds, also referred to herein as cationic steroidal anti-microbial compounds (CSAs), are synthetically produced small molecule chemical compounds that include a sterol backbone having various charged groups (e.g., amine and cationic groups) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I

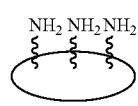

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the cellular membrane of bacteria and other microbes and inserting into the cell membrane, forming a pore that allows the leakage of ions and cytoplasmic materials that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the membrane of the bacteria.

The charged groups are responsible for disrupting the bacterial cellular membrane, and without the charged groups, the ceragenin compound cannot disrupt the membrane to cause cell death or sensitization. Examples of ceragenin compounds are shown below as Formula (I) and Formula (II), which are closely related but not identical. As will be discussed in greater detail below, the R groups of Formula (I) and Formula (II) can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring).

(I)

(II)

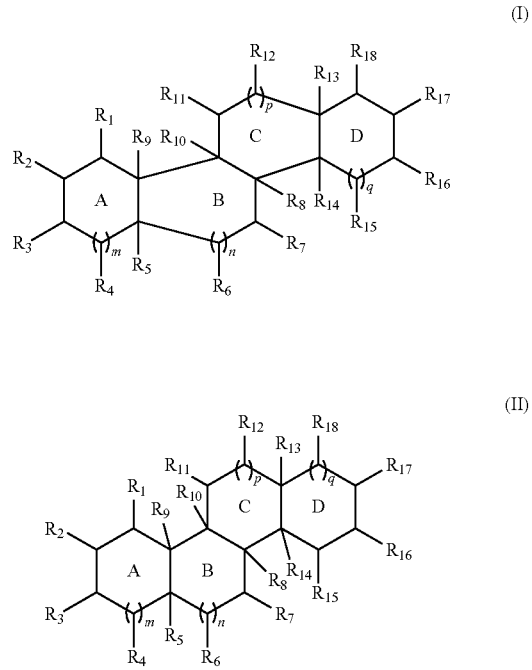

Figure 1A:
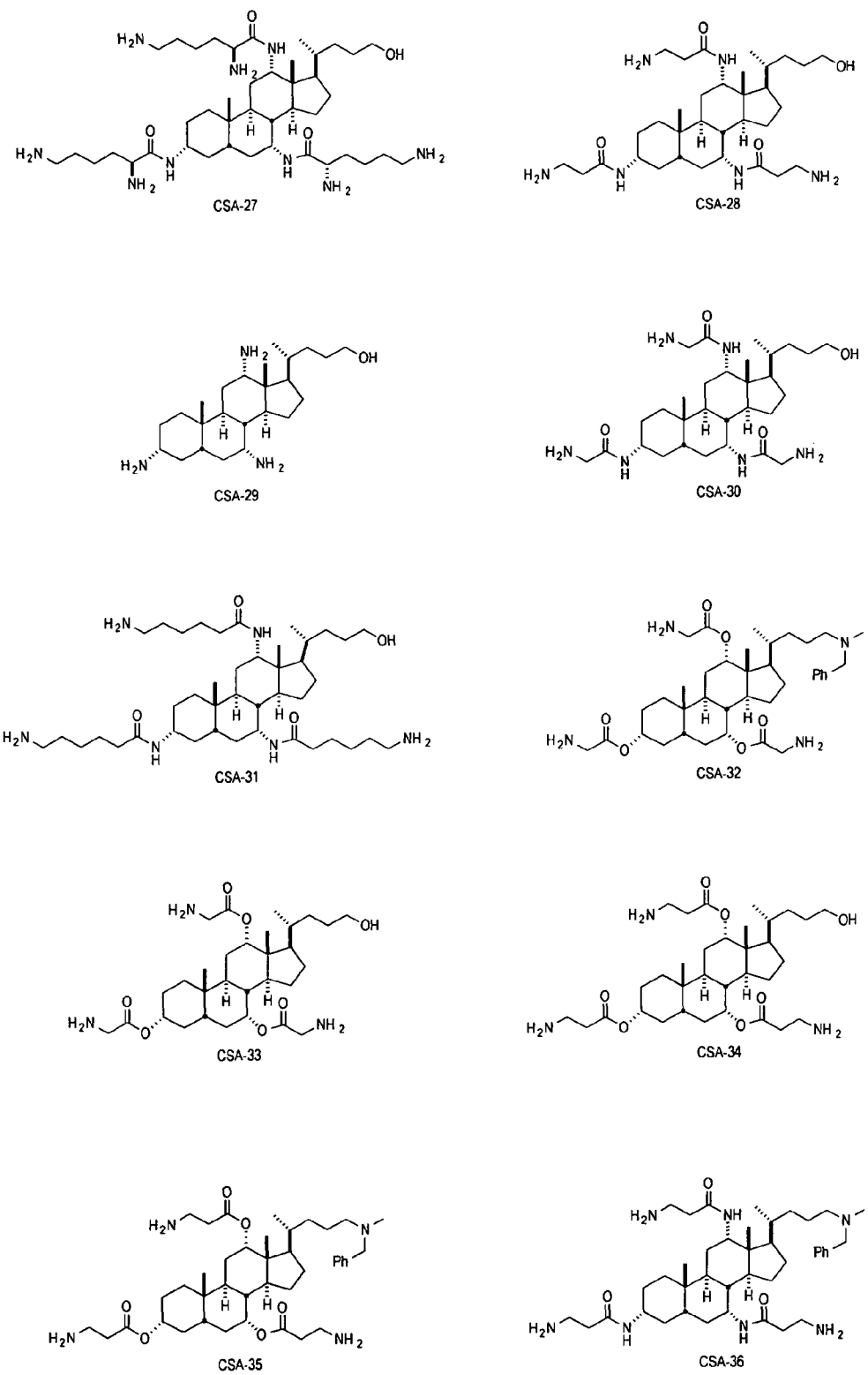
FIG. 1A illustrates exemplary hydrolysable cationic steroidal anti-microbial ("CSA") compounds.
Figure 1A:
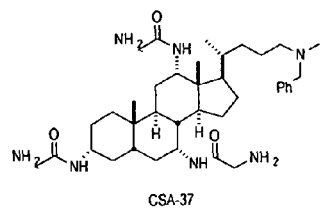
Figure 1A:
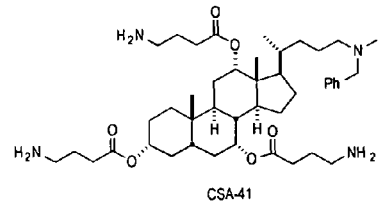
Figure 1A:
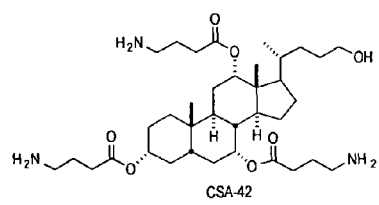
Figure 1A:
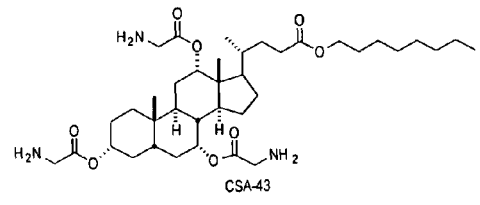
Figure 1A:
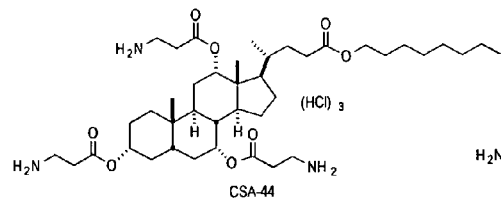
Figure 1A:
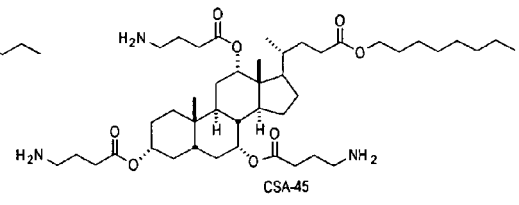
Figure 1A:
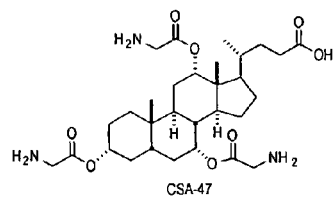
Figure 1A:
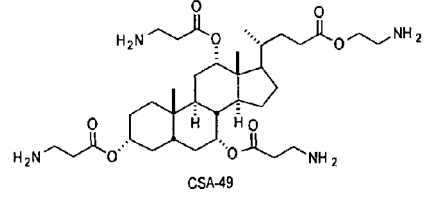
Figure 1A:
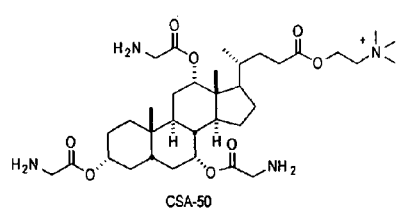
Figure 1A:
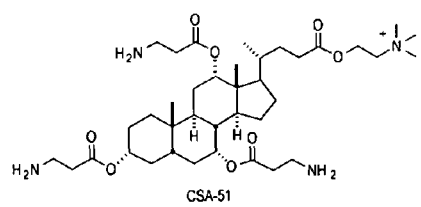
Figure 1A:
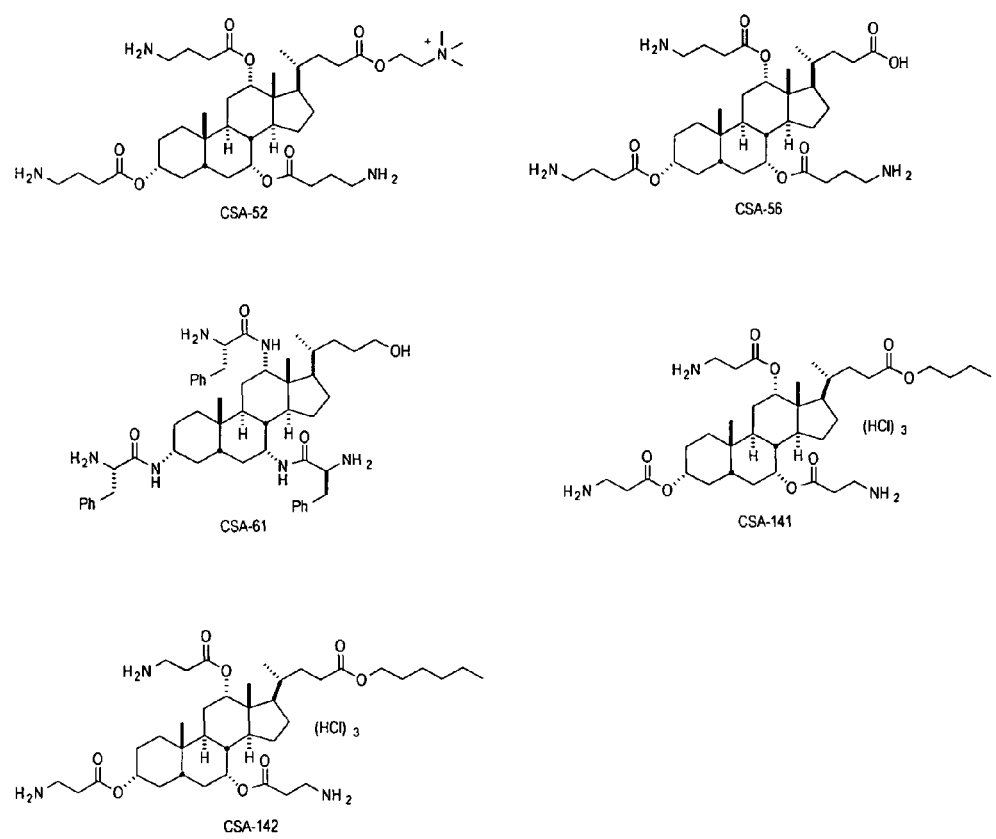
Figure 1B:
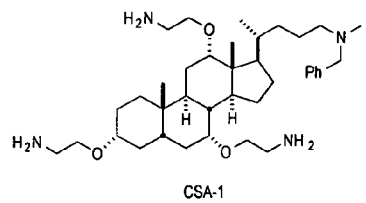
FIG. 1B illustrates exemplary non-hydrolysable CSA compounds.
Figure 1B:
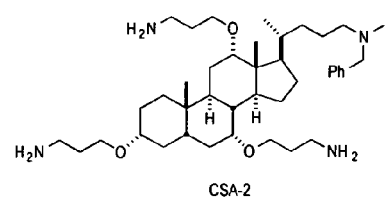
Figure 1B:
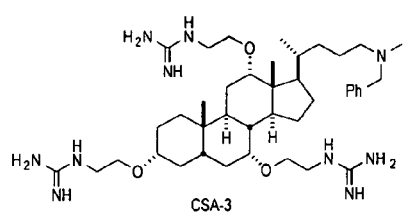
Figure 1B:
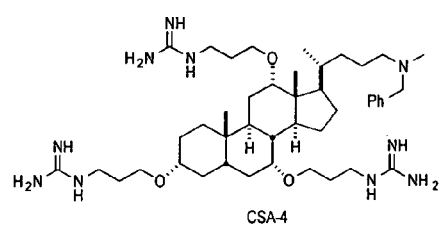
Figure 1B:
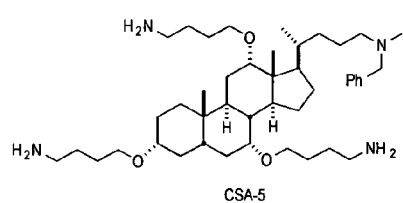
Figure 1B:
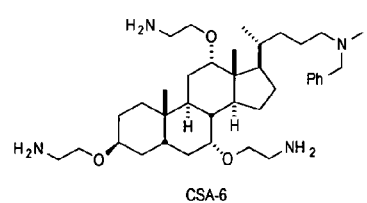
Figure 1B:
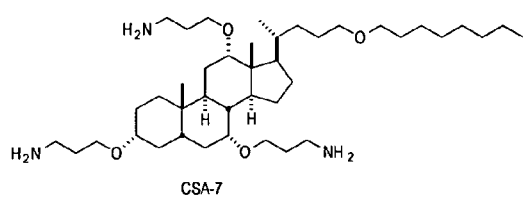
Figure 1B:
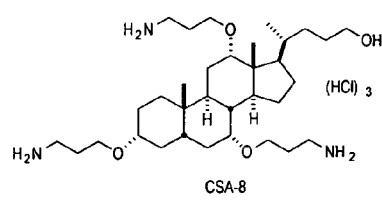
Figure 1B:
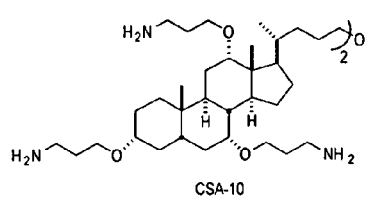
Figure 1B:
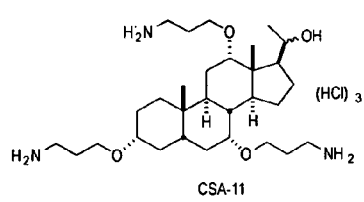
Figure 1B:
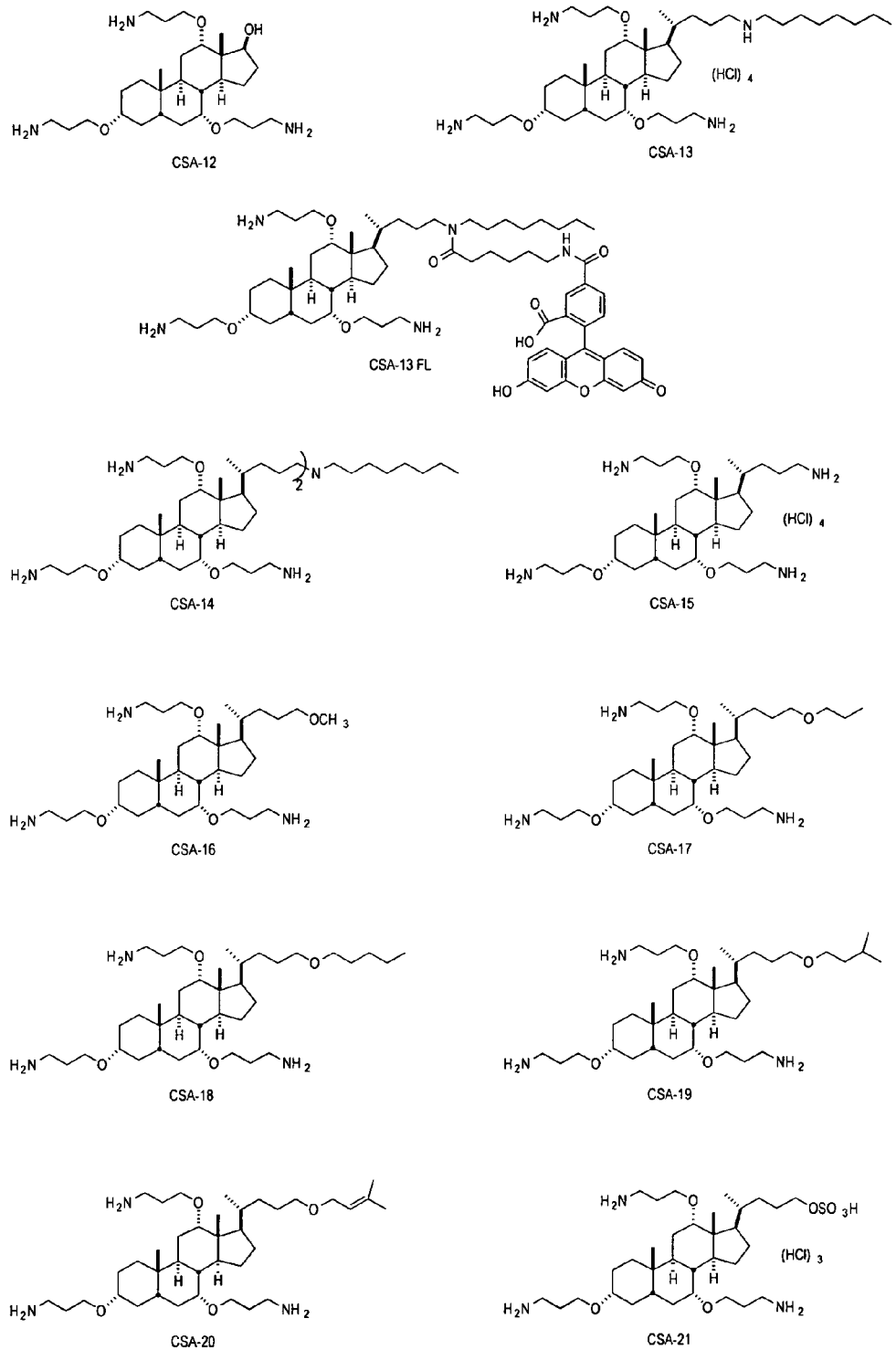
Figure 1B:
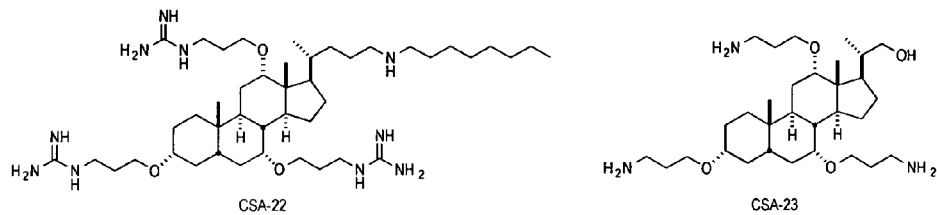
Figure 1B:
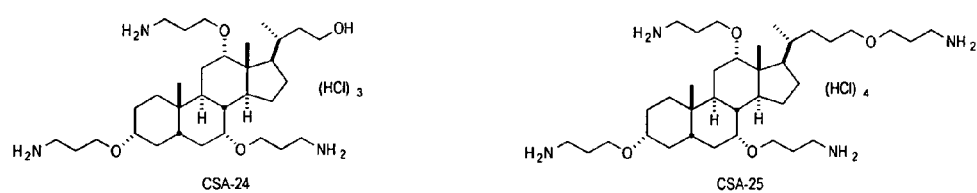
Figure 1B:
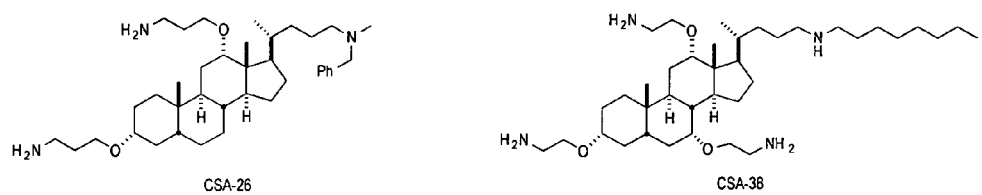
Figure 1B:
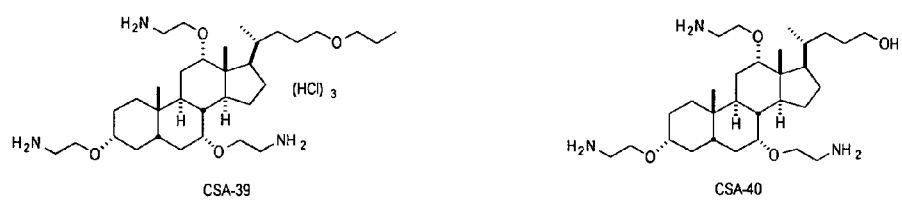
Figure 1B:
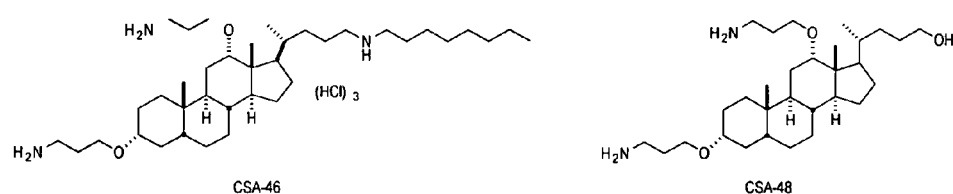
Figure 1B:
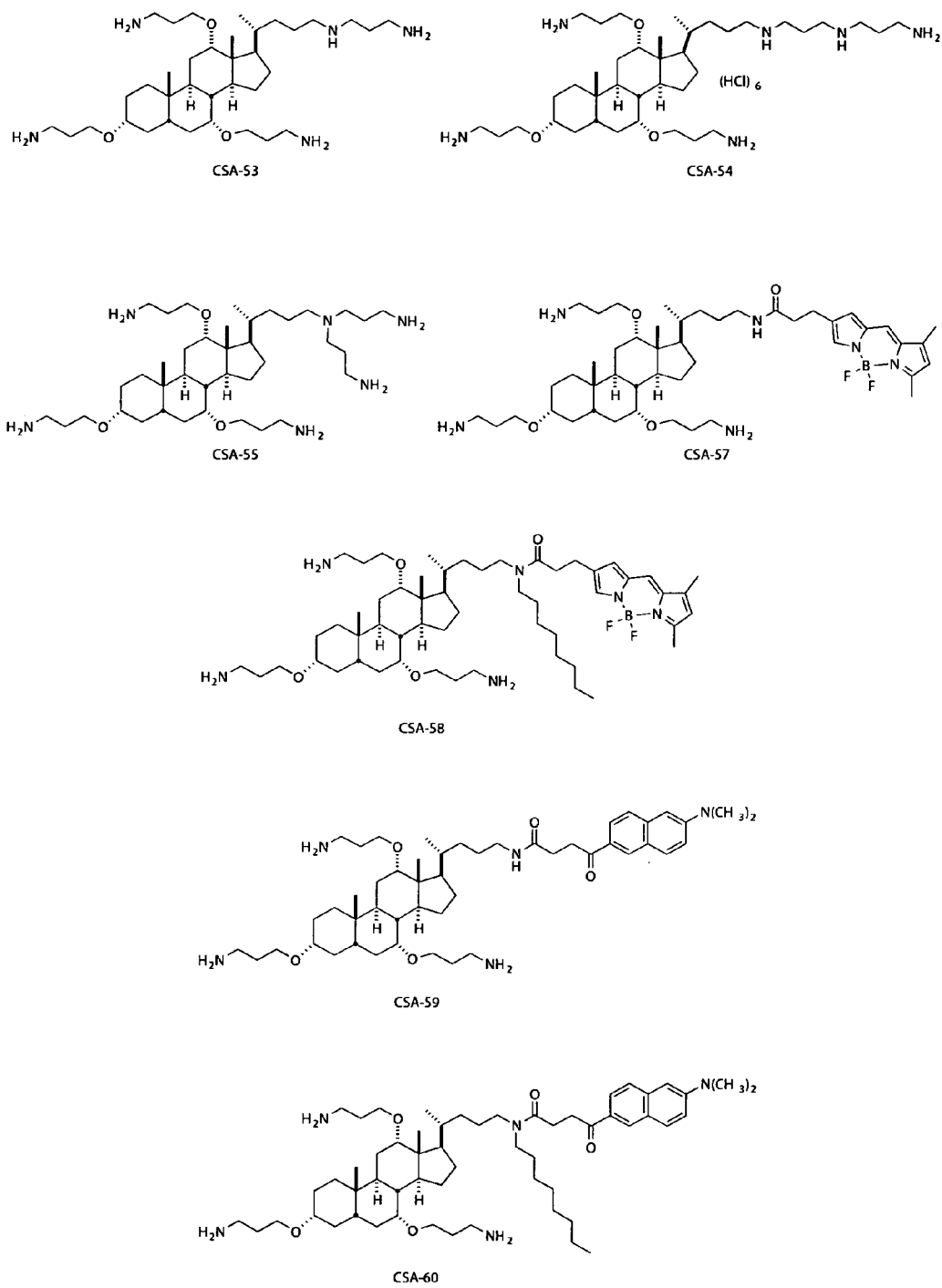
Figure 1B:
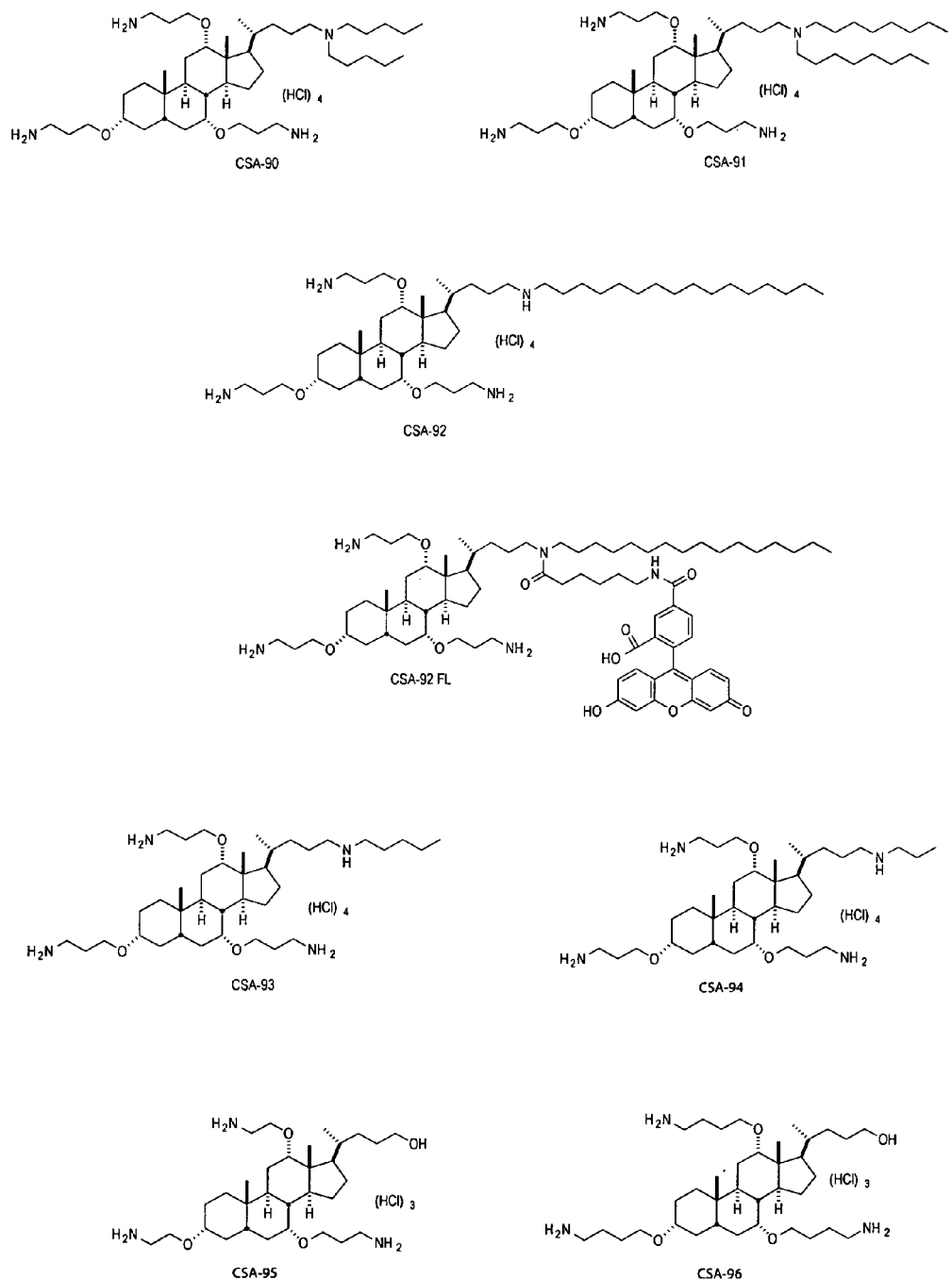
Figure 1B:
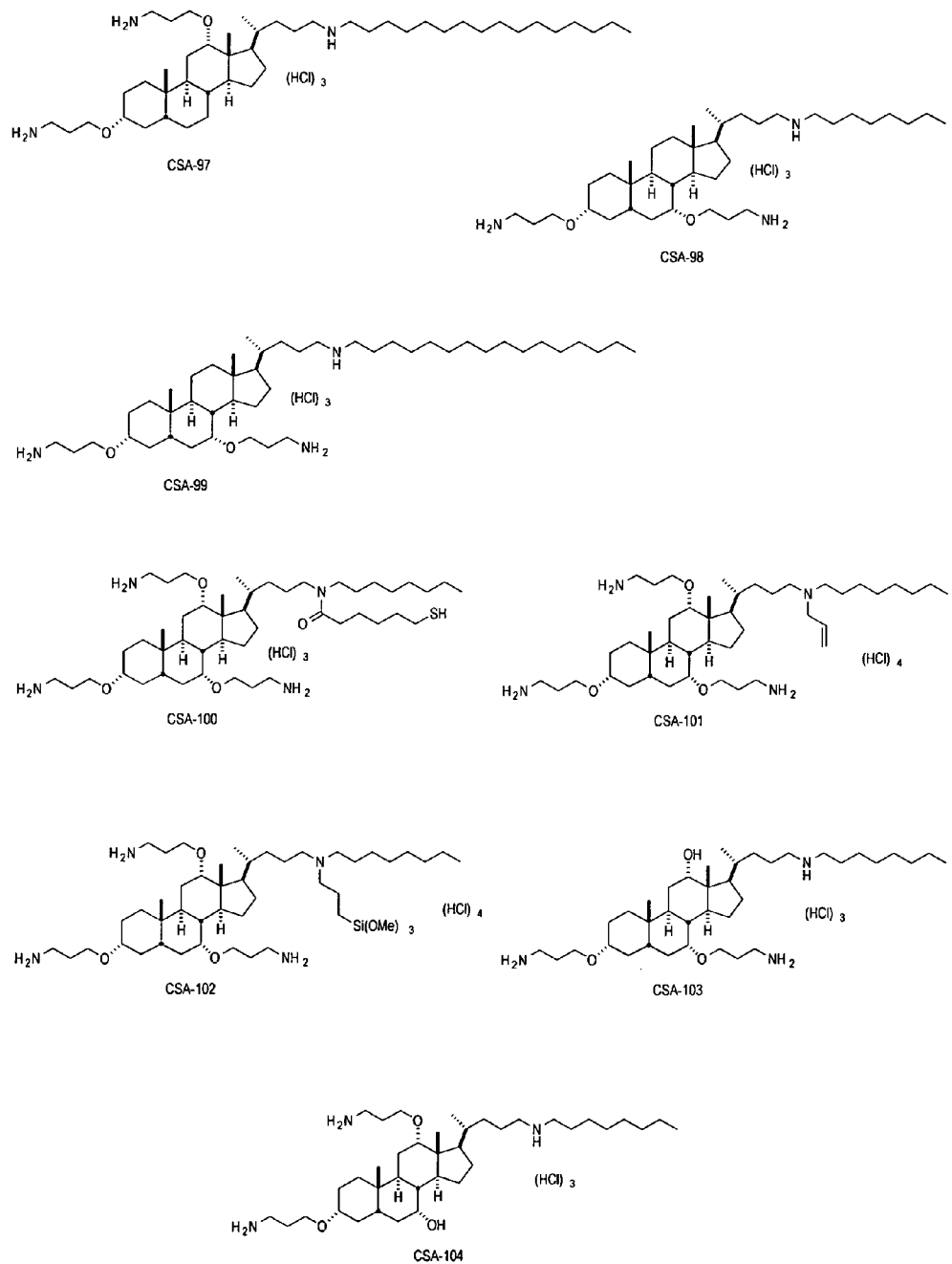
Figure 1B:
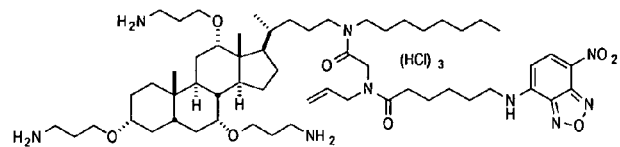
Figure 1B:
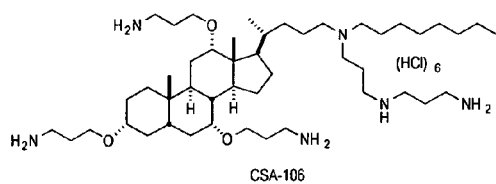
Figure 1B:
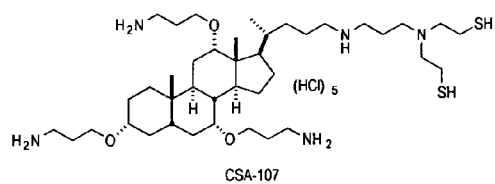
Figure 1B:
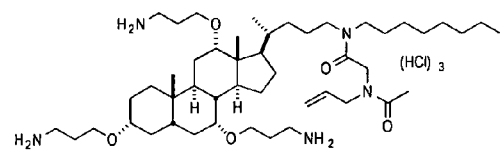
Figure 1B:
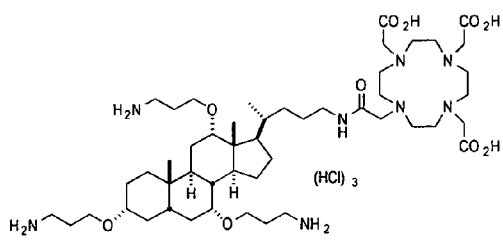
Figure 1B:
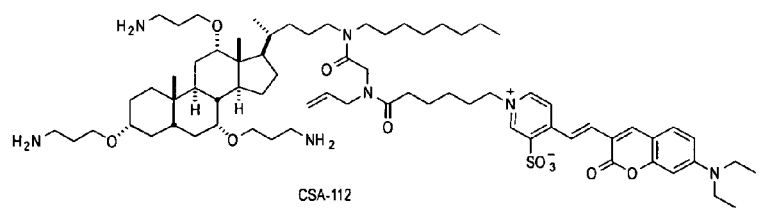
Figure 1B:
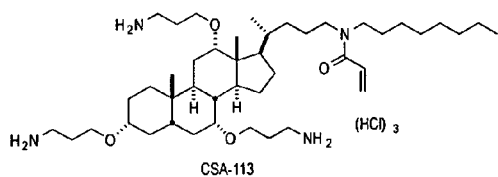
Figure 1B:
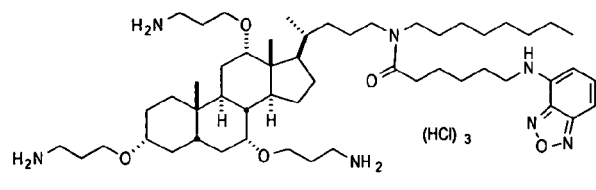
Figure 1B:
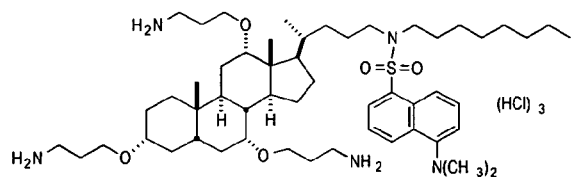
Figure 1B:
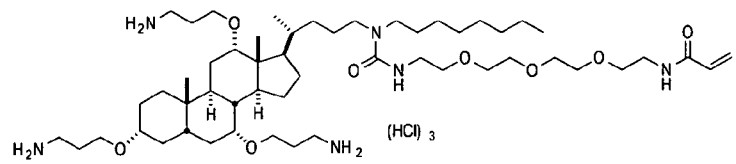
Figure 1B:
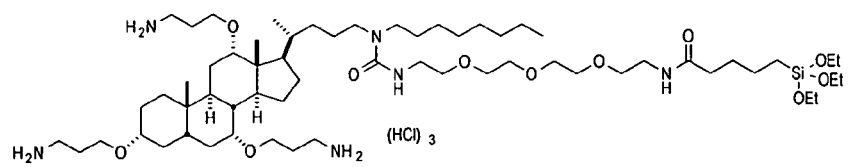
Figure 1B:
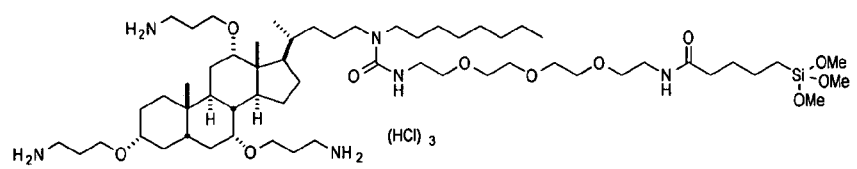
Figure 1B:
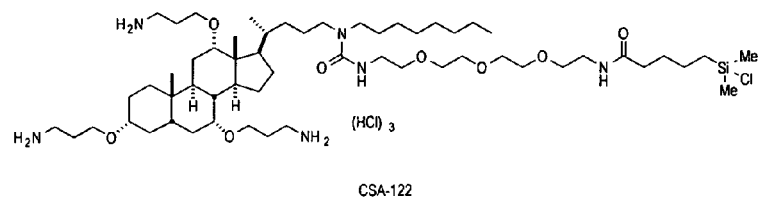
Figure 1B:
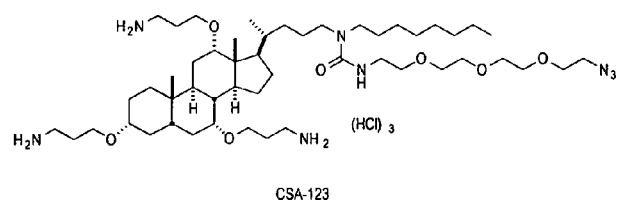
Figure 1B:
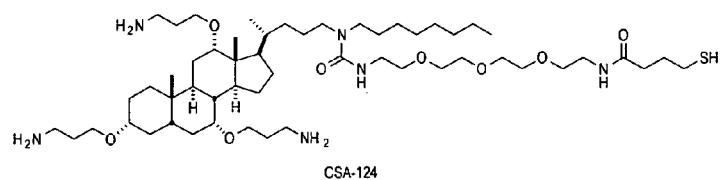
Figure 1B:
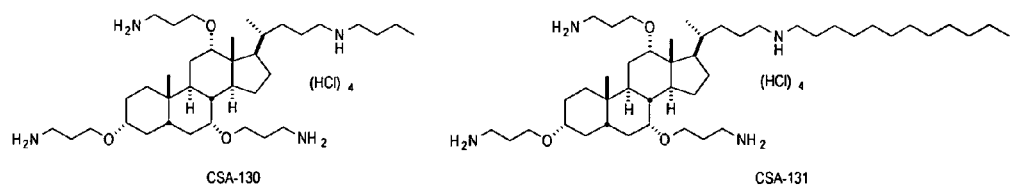
Figure 1B:
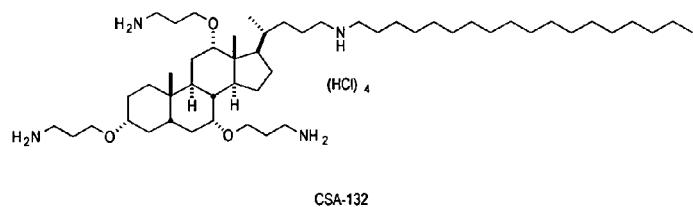
Figure 1B:
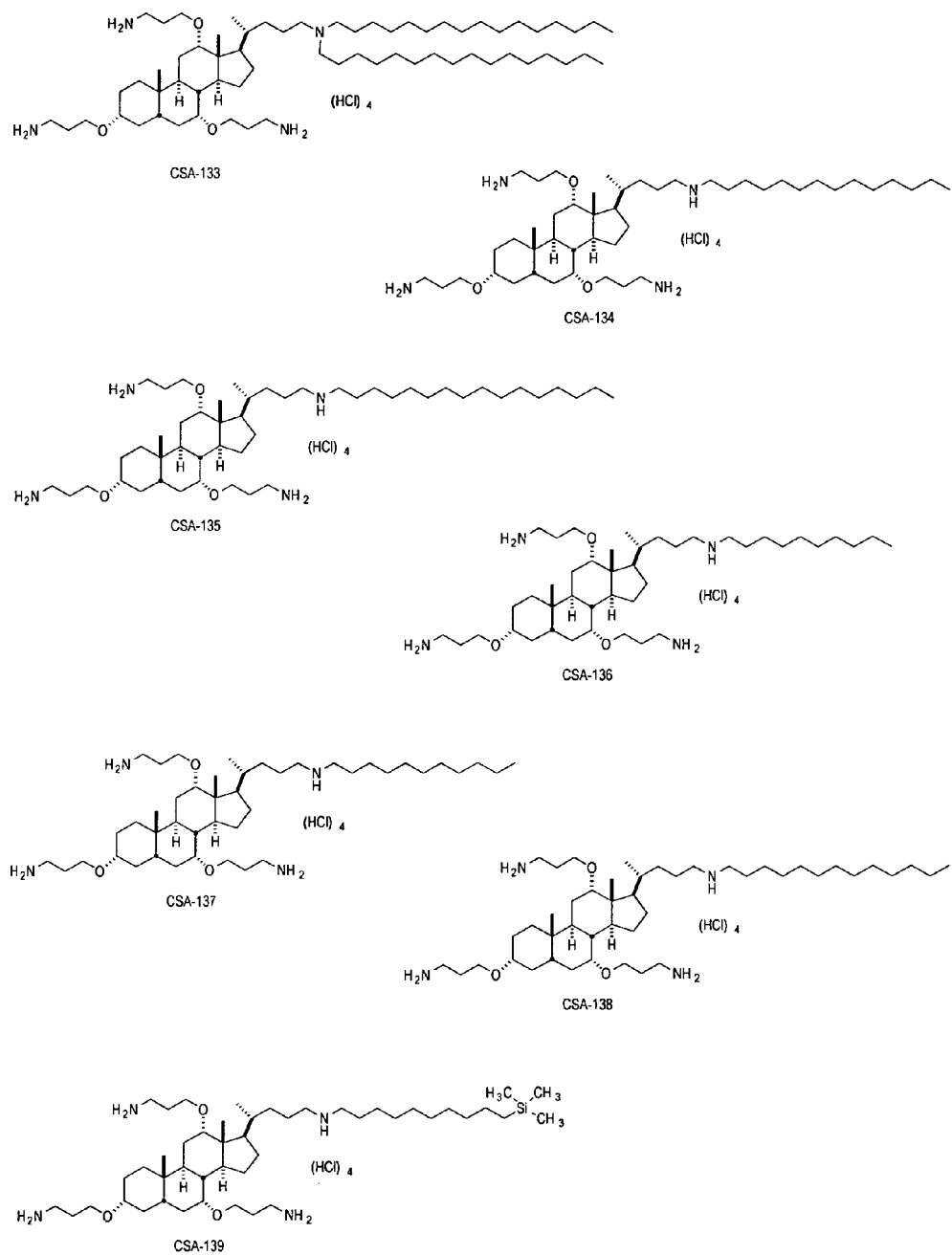

Examples of ceragenin compounds that can be incorporated into aerosol compositions are illustrated in FIGS. 1A and 1B. Typically, ceragenins of Formula (I) and Formula (II) are of two types: (1) ceragenins having cationic groups linked to the sterol backbone with hydrolysable linkages and (2) ceragenins having cationic groups linked to the sterol backbone with non-hydrolysable linkages. FIG. 1A shows examples of hydrolysable cationic steroidal anti-microbial ("CSA") compounds. FIG. 1B shows examples of non-hydrolysable CSA compounds.

Ceragenins of the first type can be "inactivated" by hydrolysis of the linkages coupling the cationic groups to the sterol backbone. For example, one type of hydrolysable linkage is an ester linkage. Esters are hydrolysed in the presence of water and base. Ceragenins of the first type are desirable, for example, where it is preferred that the ceragenins break down so that they do not buildup in the environment. Ceragenins of the second type are not readily inactivated by hydrolysis. They are desired where long-term stability in an aqueous environment is preferred. Ceragenins of the second type are preferred where long-term activity or long-term storage are needed. Ceragenins of either type can be employed in the aerosols described herein.

Suitable examples of ceragenins that may be included in the aerosols described herein include, but are not limited to, CSA-1, CSA-26, CSA-38, CSA-40, CSA-46, CSA-48, CSA-53, CSA-55, CSA-57, CSA-60, CSA-90, CSA-107, CSA-109, CSA-110, CSA-112, CSA-113, CSA-118, CSA-124, CSA-130, CSA-139, CSA-141, CSA-142, CSA-32, CSA-35, CSA-41, CSA-45, CSA-47, CSA-49-CSA-52, CSA-56, and combinations thereof.

II. Ceragenin-Containing Aerosols

As used herein, the term "aerosol" refers to a gaseous suspension of fine particles, such as a colloidal suspension of fine particles or droplets in air. Smokes and fogs are commonly known examples of aerosols. The ceragenin-containing aerosols disclosed herein may include gaseous suspensions of small liquid droplets containing ceragenins and/or gaseous suspensions of very small, e.g., micronized, ceragenin particles.

In one embodiment, a ceragenin-containing composition used to form aerosols described herein includes at least one dispersant and at least one ceragenin compound mixed with the dispersant. In one embodiment, the ceragenin compound may be added to the dispersant in an amount ranging from about 0.01 weight % ("wt %") to about 10 wt %, about 0.1 wt % to about 5 wt %, or about 0.1 wt % to about 1 wt %. Ceragenin compositions used in the aerosols described herein may be in the form of solutions, emulsions, suspensions of fine particles, and combinations thereof. Suitable examples of dispersants include, but are not limited to, water, alcohols, organic solvents, aqueous/organic emulsions, anti-clumping agents, and combinations thereof.

Ceragenin compounds are quite soluble in water and water-containing solutions. In one embodiment, a suitable example of a dispersant is water. In addition to water, the dispersant may comprise one or more alcohols, one or more surfactants, fragrances, and the like. Suitable examples of alcohols include, but are not limited to, methanol, ethanol, propanol, n-butanol, n-pentanol, and the like. Suitable examples of surfactants include, but are not limited to, anionic surfactants (e.g., sodium lauryl sulfate and alkyl-benzenesulfonates), cationic surfactants (e.g., CTAB), zwitterionic surfactants (e.g., CHAPS), and nonionic surfactants (e.g., Triton-X series detergents and polyethylene glycol monoalkyl ethers). The dispersants described herein can also include one or more non-surfactant additives (e.g., EDTA, phosphonic acids, phosphinic acids, anti-clumping agents and the like that facilitate mixing of the ceragenin with the dispersant and minimize agglomeration). Such additives can, for example, enhance the wetting properties of the above described surfactants and/or chelate metals (e.g., copper, iron, magnesium, and the like).

In addition, because some ceragenin compounds are hydrolysable in the presence of water and base (see, e.g., CSA-44), the dispersant can include stabilizing agents, such as acids, that prevent or reduce the rate of ceragenin hydrolysis. In one embodiment, for example, the ceraginin is suspended in a dispersant that further includes an acid. The ceraginin and acid are added to the dispersant in an amount sufficient to reduce the pH of the dispersant with the ceragenin compound suspended therein to a pH of about 5.5 or less. Suitable examples of acids that can be used to adjust the pH of the dispersion include, but are not limited to, acetic acid, peracetic acid, citric acid, ascorbic acid, hydrochloric acid, sulfuric acid, nitric acid, and combinations thereof.

For example, a ceragenin compound having cationic groups attached to the sterol backbone via hydrolysable linkages (see, e.g., CSA-44) may be stabilized at a pH of the ceraginin-containing dispersant of below about 4.5. Such a ceragenin compound may have a half-life of over 2 months when suspended in the dispersant at a pH of 4.5 or less. Nevertheless, such hydrolysable linkages are readily hydrolyzed in the presence of water at a pH of 7 or above. Such a ceragenin compound may have a half-life of less than 40 days when applied to a surface that raises the pH of the ceragenin containing dispersant compound to a pH of 7 or greater.

Other examples of suitable dispersants include organic solvents. Organic solvents and their properties are well-known in the arts. Suitable examples of organic solvents include, but are not limited to, pentane, cyclopentane, hexane, cyclohexane, toluene, 1,4-dioxane, chloroform, diethyl ether, dichloromethane (DCM), tetrahydrofuran (THF), ethyl acetate, acetone, dimethylformamide, acetonitrile, dimethyl sulfoxide, n-butanol, isopropanol, n-propanol, ethanol, and methanol. Solvents are used that are known to be non-toxic to biological substances which aerosols of this invention contact. In general, ceragenin compounds are quite insoluble in non-polar organic solvents, such as, but not limited to, pentane, cyclopentane, hexane, cyclohexane, toluene, 1,4-dioxane, chloroform, diethyl ether, and combinations thereof. However, such solvents can be used to disperse particulate ceragenin material that is intended to be aerosolized as a solid particulate in a dispersant. In contrast, depending on the structure of a particular ceragenin, ceragenins should be quite soluble in polar organic solvents, such as, but not limited to, dichloromethane (DCM), tetrahydrofuran (THF), ethyl acetate, acetone, dimethylformamide, acetonitrile, dimethyl sulfoxide, n-butanol, isopropanol, n-propanol, ethanol, methanol, and combinations thereof. Such polar organic solvents can be used similar to water for forming a ceragenin-containing dispersion aerosolized in fine droplets according to the present invention.

The preceding discussion of dispersants primarily relates to ceragenin-containing compositions that will be dispensed in the form of a liquid aerosol typically in the form of small droplets. Nevertheless, it is also possible to dispense an aerosolized ceragenin-containing composition in the form of a fine powder. Ceragenins can be routinely milled (e.g., ground) by a number of techniques to a surprisingly small and uniform particle size, including average particle sizes ranging from 5 nm to 200 nm, 10 nm to 150 nm, 50 nm to 125 nm, or 90 to 110 nm. Because ceragenins are relatively hygroscopic, some of the milled particles may tend to agglomerate to form larger agglomerated particles, yielding particle sizes ranging from 5 nm to 40 μm, 5 nm to 20 μm, 50 nm to 10 μm, 100 nm to 5 μm, or 1 μm to 10 μm. Particles of such sizes can be readily aerosolized.

In one embodiment, the solid, particulate ceragenin compositions that are formulated to be aerosolized may contain a number of fillers, anti-clumping agents, and the like. Suitable examples of fillers include, but are not limited to, cellulose, dibasic calcium phosphate, lactose, sucrose, glucose, mannitol, sorbitol, calcium carbonate, various excipients and magnesium stearate. Suitable examples of anti-clumping agents include, but are not limited to, tricalcium phosphate, sodium bicarbonate, sodium ferrocyanide, potassium ferrocyanide, calcium ferrocyanide, sodium silicate, silicon dioxide, calcium silicate, magnesium trisilicate, talc, sodium aluminosilicate, potassium aluminium silicate, calcium aluminosilicate, bentonite, aluminium silicate, stearic acid, and combinations thereof. Such fillers, anti-clumping agents, and other similar materials may dilute the ceragenins, prevent them from clumping together, and/or facilitate free flow of the ceragenins.

In one embodiment, aerosols include a fluidizing gas, i.e., a gas that facilitates the introduction of the ceraginin containing material in the aerosol. In one embodiment, the fluidizing gas is air. For example, an aerosol can be formed by atomizing a ceragenin-containing liquid or powder with compressed, high velocity air, heated air, and the like.

Likewise, when an aerosol is formed and the particles of the aerosol are suspended in air, the air can act to fluidize the aerosolized liquid or solid particles.

In aerosols, particle size (i.e., liquid droplet size and/or solid particle size) determines how long the aerosols discussed herein will remain suspended in the air, the number of droplets or particles that will be produced from a given volume of ceragenin-containing composition, and the size of the treated surface or area that will be covered by each droplet or particle. The following categories should be distinguished:

a. coarse sprays, with particles or droplets measuring 400 microns or more in diameter;
 b. fine sprays, with particles or droplets of from 100 to 400 microns in diameter;
 c. mists, with particles or droplets from 50 to 100 microns;
 d. fogs, and ultra-low volume (ULV) fogs or smokes with particles or droplets ranging from 0.1 to 50 microns in diameter; such fogs, and ultra-low volume (ULV) fogs or smokes may be produced by injection of the ceragenin in the form, e.g., of a powder, solution or suspension into blasts of hot air (thermal fog), or mixing such ceragenin compositions with a liquefied gas and releasing the resulting fog through a small orifice, atomizing a liquid, ceragenin-containing composition through a very fine nozzle, or spinning liquid or solid ceragenin composition off a high-speed rotor;
 f. vapors, in which all particles are less than 0.001 microns in diameter (produced by heat generators); and
 g. gases.

In one embodiment, the aerosol includes particles and/or liquid droplets capable of being suspended in air for a period of time ranging from 5 seconds 10 seconds, 30 seconds, 1 minute, 5 minutes, 10 minutes, 15 minutes, 30 minutes, 1 hour, or greater. In one embodiment, either the droplet size or the particle size should be small enough that the aerosol can remain suspended in air long enough to be distributed in a space (e.g., a room, a ventilation system, a body cavity, etc.). Preferably, the particles or droplets in the aerosols described herein have a lower size range of 0.001, 0.01, 0.1, 0.2, 0.3, 0.4, 0.5, 0.6, 0.7, 0.8, 0.9, or 1 micron in diameter, an upper size range of 5, 10, 15, 20, 25, 30, 35, 40, 45, or 50 microns, or any combination of the above listed lower and upper size ranges.

In general, smaller particles or liquid droplets have greater drift distance than larger particles. Factors that influence drift of aerosol particles and/or droplets include: (i) mean particle size; (ii) presence or absence of air currents; (iii) ambient temperature; (iv) particle discharge height & velocity; and air turbulence (velocity, direction).

In the case of liquid droplets, smaller droplets evaporate faster than larger ones under the same temperature and relative humidity conditions. This is because smaller droplets have larger facial surface area relative to their volume. Evaporation of liquid from a droplet decreases its mass, which also increases the drift distance of the droplet.

In general, ceragenin-containing aerosols having smaller particle or droplet size will disinfect a space more effectively than aerosols having larger droplet size. For example, if 1 liter of liquid is aerosolized, the total facial area of a liter's worth of 1 micron droplets will be 50 times greater than the total facial area of a liter's worth of 50 micron droplets. Likewise, in 1 liter of liquid, the number of 1 micron droplets is approximately 125,000 times greater than the number of 50 micron droplets in 1 liter. As a result, smaller particles or droplets, which remain airborne longer than larger particles, will have superior penetrability in a space. That is, the aerosols described herein are distributed in a space in much the same way that microbes are distributed in a space. Aerosols consisting of smaller droplets (e.g., 50 microns or smaller) will be better able to penetrate into all of the nooks and crannies in a space. Likewise, because aerosols consisting of smaller droplets have greater surface area than aerosols consisting of larger droplets, smaller droplets will be better able to disinfect a space and will be more cost-effective because the amount of ceragenin that is needed is significantly reduced.

III. Means for Making an Aerosol

In one embodiment, the present invention includes a device for dispensing a ceragenin-containing aerosol. The device includes a ceragenin source and a means for dispersing the ceragenin in an aerosol.

In one embodiment, the ceragenin source may include a ceragenin compound having a sterol backbone and a number of cationic groups attached thereto. In one embodiment, the ceragenin compound may be in the form of solid particles dispersed in a dispersing agent. In another embodiment, the ceraginin may be contained in liquid droplets dispersed in a dispersant. In another embodiment, the ceragenin compound may be dissolved in a dispersing agent.

Aerosols can be generated by a number of devices, including cold foggers, thermal foggers, impeller foggers, ultrasonic foggers, pressurized canisters, ultrasonic foggers, nebulizers (e.g., jet nebulizers, ultrasonic nebulizers, vibrating disc nebulizers), and other devices known in the art. All such devices are used to disperse a ceragenin-containing compound into an aerosol form. The ceraginin-containing composition may be in the form of a droplet or a powder in various sizes as described above.

A fogger is any device that creates an aerosol fog. A cold fogger (also referred to as an ultra-low-volume (ULV) fogger) generates fog droplets by injecting a high volume of air at a low pressure into a liquid and passing it through a small orifice. Many cold fogger systems are commercially available. Such systems enable droplets of a precise size to be generated. ULV foggers can dispense formulations in a more concentrated form since less liquid is required. Also, such systems can be calibrated to produce droplets of the optimum size for the type of chemical being used.

A thermal fogger is appropriately named since it is a device that uses heat to produce a fog. Ceragenins are generally quite stable at high temperature (e.g., as high as 200° C.), which makes ceragenins good candidates for thermal fogging. Many thermal fogger systems are commerically available. A thermal fogger produces a range of droplet sizes including a large number of very small droplets. This makes a thermal fogger the preferred type of equipment to reach air spaces in highly obstructed areas (e.g., in buildings). The large number of very small droplets produced in a thermally generated fog also make the fog highly visible. This can help the operator to monitor the fog and ensure thoroughness of application.

An impeller fogger uses a rotating disc to fling liquid at a diffuser, which breaks the liquid into fine droplets that float into the air.

An ultrasonic fogger generates a fog with the use of a metal diaphragm vibrating at an ultrasonic frequency that creates liquid droplets. The vibrating metal disc generally includes a piezo-electric transducer to create a high frequency mechanical oscillation in a body of liquid. The liquid tries to follow the high frequency oscillation but cannot because of its comparative weight and mass inertia. Thus, a momentary vacuum is created on the negative oscillation, causing the liquid to cavitate into vapor. The transducer follows this with a positive oscillation that creates high pressure compression waves on the liquid's surface, releasing tiny droplets into the air. This is an extremely fine mist, with droplets about one micron in diameter or less.

A pressurized canister is a device that uses a propellant (fluidizing agent) and a nozzle to generate an aerosol. For example, a room fogger uses an aerosol propellant to fill an indoor space with an aerosol. Many such devices are known in the marketplace. For example, many such devices include a release valve that can be used to automatically dispense the entire contents of the canister into a room once the release valve has been activated. Pressurized canisters can be used to dispense liquid and dry ceragini-containing compositions.

If aerosol canisters were simply filled with compressed gas, the canister would either need to be at a dangerously high pressure and require special pressure vessel design (like in gas cylinders), or the amount of gas in the can would be small, and would rapidly deplete. As a result, the propellant gas is generally the vapor of a liquid with boiling point slightly lower than room temperature. This means that inside the pressurized canister, the vapor can exist in equilibrium with its bulk liquid at a pressure that is higher than atmospheric pressure (and able to expel the cationic-containing ceragenin payload), but not dangerously high. As gas escapes, it is immediately replaced by evaporating liquid. Since the propellant exists in liquid form in the can, it should be miscible with the payload or dissolved in the payload.

Suitable examples of propellants typically include mixtures of volatile hydrocarbons, such as, but not limited to, propane, n-butane and isobutane. Dimethyl ether (DME) and methyl ethyl ether are also used. All these have the disadvantage of being flammable. Nitrous oxide and carbon dioxide are two examples of non-flammable propellants. Another type of pressurized canister that can be used to dispense a ceragenin-containing aerosol is a metered-dose inhaler (MDI). In MDIs, the ceragenin-containing composition is generally stored in solution in a pressurized canister that contains a propellant, although it may also be in a suspension. The MDI canister is attached to a plastic, hand-operated actuator. On activation, the metered-dose inhaler releases a fixed dose of ceragenin-containing medication in aerosol form. The aerosolized ceragenin-containing medication may be drawn into the lungs by activating the MDI and inhaling the aerosol into the lungs. Common propellants in MDIs are hydrofluoroalkanes (HFA): either HFA 134a (1,1,1,2,-tetrafluoroethane) or HFA 227 (1,1,1,2,3,3,3-heptafluoropropane) or combinations of the two.

Another alternative is a dry powder inhaler (DPI). A DPI is a device that can be used to deliver a medication to the lungs in the form of a dry powder. The ceragenin-containing medication is commonly held either in a capsule for manual loading or a proprietary form from inside the inhaler. Once loaded or actuated, the operator puts the mouthpiece of the inhaler into their mouth and takes a deep inhalation, holding their breath for 5-10 seconds. There are a variety of such devices. The dose that can be delivered is typically less than a few tens of milligrams. DPIs are commonly used to treat respiratory diseases such as asthma, bronchitis, emphysema and COPD and ban be deployed to deliver ceragenin-containing compounds, especially to biological surfaces.

Nebulizers typically use compressed air or ultrasonic power to break up liquids into small aerosol droplets. Such devices are commonly used for inhalable medications, but they can be adapted for fumigating a wider area. The most commonly used nebulizers are jet nebulizers. Jet nebulizers are connected by tubing to a compressor that causes compressed air to flow at high velocity through a liquid to turn it into an aerosol. Ultrasonic wave nebulizers have an electronic oscillator that generates a high frequency ultrasonic wave, which causes the mechanical vibration of a piezoelectric element. This vibrating element is in contact with a liquid reservoir and its high frequency vibration is sufficient to produce a vapor mist. Another type of nebulizer is the ultrasonic vibrating mesh nebulizer. With this technology a mesh/membrane with a large number of holes (e.g., 1000-7000 laser drilled holes) vibrates at the top of the liquid reservoir, and thereby pressures out a mist of very fine droplets through the holes. This technology is more efficient than having a vibrating piezoelectric element at the bottom of the liquid reservoir. Such nebulizers can be used to deliver ceragenin compounds into spaces such as rooms or to biological surfaces.

Figure 2:
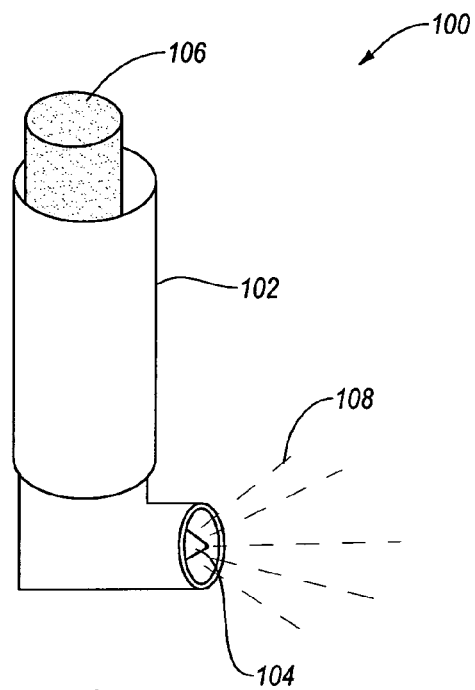
FIG. 2 illustrates a hand held inhaler for delivering a ceragenin compound.
Figure 3:
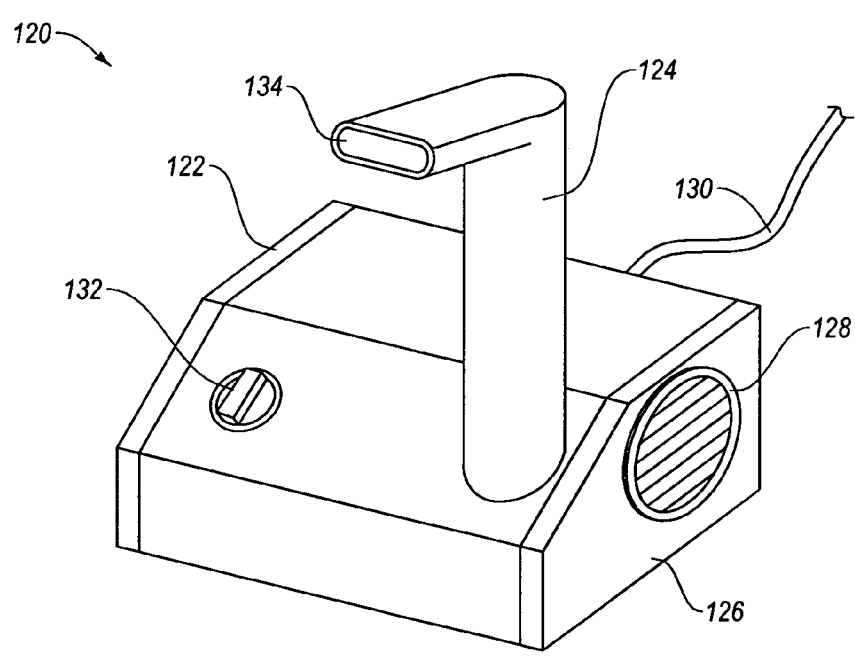
FIG. 3 illustrates a nebulizer for delivering a ceragenin compound.
Figure 4:
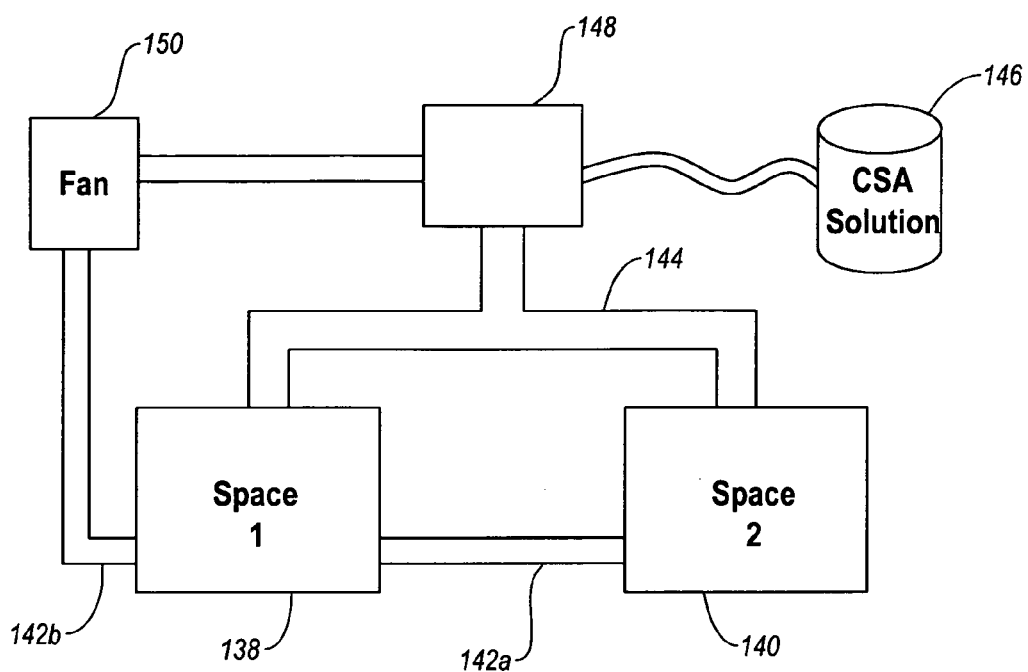
FIG. 4 illustrates a ventilation system for delivering a ceragenin compound.

FIGS. 2-4 illustrate example devices and systems that can be used to generate an aerosol of a ceragenin. FIG. 2 illustrates a hand held inhaler 100 for delivering a ceragenin compound. Inhaler 100 has a housing 102 that houses a canister 106. Canister 106 includes a propellant and a pharmacologically effective amount of a ceragenin compound. A nozzle 104 is in fluid communication with a valve of the canister (not shown) that, when actuated, causes a metered amount of spray to be aerosolized. Housing 102 is preferably configured to deliver an aerosol spray 108 to the mouth of a patient, but other configurations may be used.

FIG. 3 illustrates a nebulizer 120, which includes a pump 122 that receives air through an air inlet 128 and delivers the air through a ceragenin fluid reservoir (not shown) disposed inside a housing 126. The nebulized air travels through a stem 124 and exits an outlet 134 for inhalation by a patient and/or distribution to a room or other space. Nebulizer 120 can be powered through a cord 130. In addition, a supplemental fluid source 132 can be used to deliver oxygen and/or a ceragenin compound to be nebulized.

FIG. 4 illustrates an in-building fogger system 136. Fogger system 136 includes a plurality of spaces (space 138 and space 140) that receive air through ductwork 144. Ductwork 144 may include forced air, such as provided by a blower 150. A fogger or other device 148 is configured to receive a ceragenin fluid 146 and fluidize a ceragenin composition therein into the air being supplied into spaces 138 and 140. Fogger system 136 may also include return ductwork 142a, 142b.

IV. Methods for Delivering a Ceragenin to a Space

In one embodiment, a method for delivering a ceragenin to a space is includes: (1) dispersing a ceragenin-containing aerosol in a space, wherein the space includes one or more microbe-exposed surfaces; (2) contacting the one or more microbe-exposed surfaces in the space with the aerosol, and (3) depositing the ceragenin compound on the one or more microbe-exposed surfaces.

In one embodiment, the ceragenin deposited on the one or more microbe-exposed surfaces can be used to kill microbes on the surfaces. Likewise, because ceragenins are typically active or capable of being activated for an extended period of time (e.g., up to 1 day, up to five days, up to 10 days, up to 1 month, up to 2 months, etc.), the ceragenins can kill microbes that come into contact with the one or more microbe-exposed surfaces after the ceragenins are deposited. In addition, ceragenins can kill microbes encountered in the air in the space.

In some cases, it may be desirable to eliminate the ceragenin compound in a space or on a surface after giving it sufficient time to kill harmful bacteria. An example of a suitable technique for eliminating aerosol particles from a space that has been treated is to filter the air using an ionizer. The ionizer can increase the charge on the particles and cause them to rapidly precipitate from the gaseous medium and/or accumulate on surfaces.

In one embodiment, the aerosol composition may be formulated such that the ceragenin breaks down over time after contacting the one or more surfaces. For example, the ceragenin compound may be formulated to have a half-life of less than 40 days after contacting the one or more surfaces in the space. The selected breakdown of ceragenin over time can be achieved using acids or buffer to stabilize a ceragenin with a hydrolysable linkage as discussed herein.

According to the present disclosure, a surface exposed to one or more microbes can be essentially any surface that is either known to be or suspected to be contaminated by or suspected to be exposed to one or more microbes. Examples of microbes that may contaminate the surface include, but are not limited to, bacteria, fungi, and viruses. Such a method can be used to disinfect spaces including, but not limited to residential spaces, hospital spaces, food preparation facility spaces (e.g., restaurants or factories), food packaging facility spaces, and ventilation system spaces (e.g., air ducts).

In one embodiment, the one or more surfaces in the space are selected from the group consisting of metallic surfaces, ceramic surfaces, wooden surfaces, polymer surfaces, and combinations thereof. In one embodiment, at least one of the metallic surface, ceramic surface, wooden surface, glass surface, or polymer surface includes at least one of a bathroom surface, kitchen surface, food preparation surface, food packaging surface, hospital surface, air handling surface, or laboratory surface.

In a specific example, aerosols described herein can be used to fumigate and disinfect a surgical suite or a similar area in a hospital. For example, many antibiotic resistant bacteria reside in hospitals and, as a result, hospital-acquired infections are a nagging problem in the medical field. Because ceragenins are effective against essentially all bacteria, including multi-drug-resistant bacteria, because aerosols have the ability to penetrate a space, because ceragenins have a long-acting antibacterial effect, and because ceragenins are non-toxic to humans and other animals, the ceragenin aerosols described herein are particularly well suited for disinfecting hospital spaces. Likewise, they are well suited for disinfecting residential spaces, food preparation facility spaces (e.g., restaurants or factories), a food packaging facility spaces, and ventilation system spaces (e.g., air ducts).

In another embodiment, the ceragenin-containing aerosols may be used to treat a biological surface that may include at least one of a respiratory system surface of a human or other animal. In a specific example, ceragenin-containing aerosols may be inhaled into the lungs or the nasal passages to treat a respiratory infection such as, but not limited to, pneumonia and sinus infections. Because ceragenins are non-toxic to humans and animals, and ceragenins do not adversely affect human or animal cells, ceragenins are particularly well suited for localized treatment of bodily infections. They may be generally superior to the use of systemic antibiotics for treatment of localized infections.

In one embodiment, the method further includes dispersing the aerosol substantially evenly in the space such that the composition can contact a number of spaced apart microbe-exposed surfaces in the space. That is, because of the small droplet or particle size of the aerosol, the aerosol can contact a number of spaced apart microbe-exposed surfaces in the space. Likewise, because the aerosol diffuses through the space or is actively distributed in the space by essentially the same mechanism that bacteria and other microbes are distributed in a space, the aerosol can contact essentially every nook and cranny in a space where microbes may lurk.

V. Ceragenin Compounds

Example ceragenin compounds used to make aerosols can have a formula as set forth in Formula (I):

where m, n, p, and q are independently 0 or 1; $R^1$-$R^{18}$ represent substituents that are attached to the indicated atom on the steroid backbone (i.e., steroid group); and at least two, preferably at least three, of $R^1$-$R^{18}$ each include a cationic group.

In one embodiment, rings A, B, C, and D are independently saturated, or are fully or partially unsaturated, provided that at least two of rings A, B, C, and D are saturated; m, n, p, and q are independently 0 or 1; $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted alkyl, substituted or unsubstituted hydroxyalkyl, substituted or unsubstituted alkyloxyalkyl, substituted or unsubstituted alkylcarboxyalkyl, substituted or unsubstituted alkylaminoalkyl, substituted or unsubstituted alkylaminoalkylamino, substituted or unsubstituted alkylaminoalkylaminoalkylamino, a substituted or unsubstituted aminoalkyl, a substituted or unsubstituted aryl, a substituted or unsubstituted arylaminoalkyl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkyloxyalkyl, a substituted or unsubstituted aminoalkylcarboxy, a substituted or unsubstituted aminoalkylaminocarbonyl, a substituted or unsubstituted aminoalkylcarboxamido, a substituted or unsubstituted di(alkyl)aminoalkyl, a substituted or unsubstituted C-carboxyalkyl, $H_2N$—$HC(Q_5)$-$C(O)$—O—, $H_2N$—$HC(Q_5)$-$C(O)$—$N(H)$—, substituted or unsubstituted azidoalkyloxy, substituted or unsubstituted cyanoalkyloxy, P.G.-HN—$HC(Q_5)$-$C(O)$—O—, substituted or unsubstituted guanidinoalkyloxy, substituted or unsubstituted quaternaryammoniumalkylcarboxy, and substituted or unsubstituted guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted alkyl, substituted or unsubstituted hydroxyalkyl, substituted or unsubstituted alkyloxyalkyl, a substituted or unsubstituted aminoalkyl, a substituted or unsubstituted aryl, substituted or unsubstituted haloalkyl, substituted or unsubstituted alkenyl, substituted or unsubstituted alkynyl, oxo, a linking group attached to a second steroid, a substituted or unsubstituted aminoalkyloxy, a substituted or unsubstituted aminoalkylcarboxy, a substituted or unsubstituted aminoalkylaminocarbonyl, a substituted or unsubstituted di(alkyl)aminoalkyl, a substituted or unsubstituted C-carboxyalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN—HC($Q_5$)-C(O)—O—, substituted or unsubstituted guanidinoalkyloxy, and substituted or unsubstituted guanidinoalkylcarboxy, where $Q_5$ is a side chain of any amino acid, P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted aminoalkyl, a substituted or unsubstituted aminoalkyloxy, substituted or unsubstituted alkylcarboxyalkyl, substituted or unsubstituted alkylaminoalkylamino, substituted or unsubstituted alkylaminoalkylaminoalkylamino, a substituted or unsubstituted aminoalkylcarboxy, a substituted or unsubstituted arylaminoalkyl, a substituted or unsubstituted aminoalkyloxyaminoalkylaminocarbonyl, a substituted or unsubstituted aminoalkylaminocarbonyl, a substituted or unsubstituted aminoalkylcarboxyamido, a substituted or unsubstituted quaternaryammoniumalkylcarboxy, a substituted or unsubstituted di(alkyl)aminoalkyl, a substituted or unsubstituted C-carboxyalkyl, $H_2N-HC(Q_5)-C(O)-O-$, $H_2N-HC(Q_5)-C(O)-N(H)-$, substituted or unsubstituted azidoalkyloxy, substituted or unsubstituted cyanoalkyloxy, P.G.-HN—HC($Q_5$)-C(O)—O—, substituted or unsubstituted guanidinoalkyloxy, a substituted or unsubstituted guanidinoalkylcarboxy, or a pharmaceutically acceptable salt thereof.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino-($C_1$-$C_{18}$) alkylamino, a substituted or unsubstituted ($C_1$-$C_{18}$) aminoalkyl, a substituted or unsubstituted aryl, a substituted or unsubstituted arylamino-($C_1$-$C_{18}$) alkyl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkyloxy-($C_1$-$C_{18}$) alkyl, a substituted or unsubstituted ($C_1$-$C_{18}$) aminoalkylcarboxy, a substituted or unsubstituted ($C_1$-$C_{18}$) aminoalkylaminocarbonyl, a substituted or unsubstituted ($C_1$-$C_{18}$) aminoalkylcarboxamido, a substituted or unsubstituted di($C_1$-$C_{18}$ alkyl)aminoalkyl, a substituted or unsubstituted C-carboxy($C_1$-$C_{18}$)alkyl, $H_2N-HC(Q_5)-C(O)-O-$, $H_2N-HC(Q_5)-C(O)-N(H)-$, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O—, substituted or unsubstituted ($C_1$-$C_{18}$) guanidinoalkyloxy, substituted or unsubstituted ($C_1$-$C_{18}$) quaternaryammoniumalkylcarboxy, and substituted or unsubstituted ($C_1$-$C_{18}$) guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valence of the carbon atom at that site, or $R_5$, $R_8$, $R_9$, $R_{10}$, $R_{13}$, and $R_{14}$ are independently selected from the group consisting of hydrogen, hydroxyl, a substituted or unsubstituted ($C_1$-$C_{18}$) alkyl, substituted or unsubstituted ($C_1$-$C_{18}$) hydroxyalkyl, substituted or unsubstituted ($C_1$-$C_{18}$) alkyloxy-($C_1$-$C_{18}$) alkyl, a substituted or unsubstituted ($C_1$-$C_{18}$) aminoalkyl, a substituted or unsubstituted aryl, substituted or unsubstituted ($C_1$-$C_{18}$) haloalkyl, substituted or unsubstituted ($C_2$-$C_6$) alkenyl, substituted or unsubstituted ($C_2$-$C_6$) alkynyl, oxo, a linking group attached to a second steroid, a substituted or unsubstituted ($C_1$-$C_{18}$) aminoalkyloxy, a substituted or unsubstituted ($C_1$-$C_{18}$) aminoalkylcarboxy, a substituted or unsubstituted ($C_1$-$C_{18}$) aminoalkylaminocarbonyl, di($C_1$-$C_{18}$ alkyl) aminoalkyl, a substituted or unsubstituted C-carboxy($C_1$-$C_{18}$)alkyl, $H_2N-HC(Q_5)-C(O)-O-$, $H_2N-HC(Q_5)-C(O)-N(H)-$, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O—, substituted or unsubstituted ($C_1$-$C_{18}$) guanidinoalkyloxy, and substituted or unsubstituted ($C_1$-$C_{18}$) guanidinoalkylcarboxy, where Q5 is a side chain of any amino acid, and P.G. is an amino protecting group; provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{18}$) aminoalkyl, a substituted or unsubstituted ($C_1$-$C_{18}$) aminoalkyloxy, substituted or unsubstituted ($C_1$-$C_{18}$) alkylcarboxy-($C_1$-$C_{18}$) alkyl, substituted or unsubstituted ($C_1$-$C_{18}$) alkylamino-($C_1$-$C_{18}$) alkylamino, substituted or unsubstituted ($C_1$-$C_{18}$) alkylamino-($C_1$-$C_{18}$) alkylamino ($C_1$-$C_{18}$) alkylamino, a substituted or unsubstituted ($C_1$-$C_{18}$) aminoalkylcarboxy, a substituted or unsubstituted arylamino ($C_1$-$C_{18}$) alkyl, a substituted or unsubstituted ($C_1$-$C_{18}$) aminoalkyloxy ($C_1$-$C_{18}$) aminoalkylaminocarbonyl, a substituted or unsubstituted ($C_1$-$C_{18}$) aminoalkylaminocarbonyl, a substituted or unsubstituted ($C_1$-$C_{18}$) aminoalkylcarboxyamido, a substituted or unsubstituted ($C_1$-$C_{18}$) quaternaryammoniumalkylcarboxy, substituted or unsubstituted di($C_1$-$C_{18}$ alkyl)aminoalkyl, a substituted or unsubstituted C-carboxy($C_1$-$C_{18}$) alkyl, $H_2N-HC(Q_5)-C(O)-O-$, $H_2N-HC(Q_5)-C(O)-N(H)-$, substituted or unsubstituted ($C_1$-$C_{18}$) azidoalkyloxy, substituted or unsubstituted ($C_1$-$C_{18}$) cyanoalkyloxy, P.G.-HN—HC($Q_5$)-C(O)—O—, substituted or unsubstituted ($C_1$-$C_{18}$) guanidinoalkyloxy, a substituted or unsubstituted ($C_1$-$C_{18}$) guanidinoalkylcarboxy, or a pharmaceutically acceptable salt thereof.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$) alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted $(C_1\text{-}C_{18})$ aminoalkylcarboxamido, an unsubstituted di$(C_1\text{-}C_{18}$ alkyl)aminoalkyl, an unsubstituted C-carboxy$(C_1\text{-}C_{18})$alkyl, unsubstituted $(C_1\text{-}C_{18})$ guanidinoalkyloxy, unsubstituted $(C_1\text{-}C_{18})$ quaternaryammoniumalkylcarboxy, and unsubstituted $(C_1\text{-}C_{18})$ guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, an unsubstituted $(C_1\text{-}C_{18})$ alkyl, unsubstituted $(C_1\text{-}C_{18})$ hydroxyalkyl, unsubstituted $(C_1\text{-}C_{18})$ alkyloxy-$(C_1\text{-}C_{18})$ alkyl, unsubstituted $(C_1\text{-}C_{18})$ alkylcarboxy-$(C_1\text{-}C_{18})$ alkyl, unsubstituted $(C_1\text{-}C_{18})$ alkylamino-$(C_1\text{-}C_{18})$ alkyl, unsubstituted $(C_1\text{-}C_{18})$ alkylamino-$(C_1\text{-}C_{18})$ alkylamino, unsubstituted $(C_1\text{-}C_{18})$ alkylamino-$(C_1\text{-}C_{18})$ alkylamino-$(C_1\text{-}C_{18})$ alkylamino, an unsubstituted $(C_1\text{-}C_{18})$ aminoalkyl, an unsubstituted aryl, an unsubstituted aryl amino-$(C_1\text{-}C_{18})$ alkyl, oxo, an unsubstituted $(C_1\text{-}C_{18})$ aminoalkyloxy, an unsubstituted $(C_1\text{-}C_{18})$ aminoalkyloxy-$(C_1\text{-}C_{18})$ alkyl, an unsubstituted $(C_1\text{-}C_{18})$ aminoalkylcarboxy, an unsubstituted $(C_1\text{-}C_{18})$ aminoalkylaminocarbonyl, an unsubstituted $(C_1\text{-}C_{18})$ aminoalkylcarboxamido, an unsubstituted di$(C_1\text{-}C_{18}$ alkyl)aminoalkyl, an unsubstituted C-carboxy$(C_1\text{-}C_{18})$alkyl, unsubstituted $(C_1\text{-}C_{18})$ guanidinoalkyloxy, unsubstituted $(C_1\text{-}C_{18})$ quaternaryammoniumalkylcarboxy, and unsubstituted $(C_1\text{-}C_{18})$ guanidinoalkyl carboxy; provided that at least two or three of $R_{1\text{-}4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted $(C_1\text{-}C_{18})$ alkyl, unsubstituted $(C_1\text{-}C_{18})$ hydroxyalkyl, unsubstituted $(C_1\text{-}C_{18})$ alkyloxy-$(C_1\text{-}C_{18})$ alkyl, unsubstituted $(C_1\text{-}C_{18})$ alkylcarboxy-$(C_1\text{-}C_{18})$ alkyl, unsubstituted $(C_1\text{-}C_{18})$ alkylamino-$(C_1\text{-}C_{18})$alkyl, unsubstituted $(C_1\text{-}C_{18})$ alkylamino-$(C_1\text{-}C_{18})$ alkylamino, unsubstituted $(C_1\text{-}C_{18})$ alkylamino-$(C_1\text{-}C_{18})$ alkylamino-$(C_1\text{-}C_{18})$ alkylamino, an unsubstituted $(C_1\text{-}C_{18})$ aminoalkyl, an unsubstituted aryl, an unsubstituted arylamino-$(C_1\text{-}C_{18})$ alkyl, oxo, an unsubstituted $(C_1\text{-}C_{18})$ aminoalkyloxy, an unsubstituted $(C_1\text{-}C_{18})$ aminoalkyloxy-$(C_1\text{-}C_{18})$ alkyl, an unsubstituted $(C_1\text{-}C_{18})$ aminoalkylcarboxy, an unsubstituted $(C_1\text{-}C_{18})$ aminoalkylaminocarbonyl, an unsubstituted $(C_1\text{-}C_{18})$ aminoalkylcarboxamido, an unsubstituted di$(C_1\text{-}C_{18}$ alkyl)aminoalkyl, an unsubstituted C-carboxy$(C_1\text{-}C_{18})$alkyl, unsubstituted $(C_1\text{-}C_{18})$ guanidinoalkyloxy, unsubstituted $(C_1\text{-}C_{18})$ quaternaryammoniumalkylcarboxy, unsubstituted $(C_1\text{-}C_{18})$ guanidinoalkyl carboxy, or a pharmaceutically acceptable salt thereof.

According to other embodiments, the ceragenin compounds used to make aerosols can have a structure as shown in Formula (II), which is closely related to, but not identical to, Formula (I):

(II)

where each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1 (i.e., each ring may independently be 5-membered or 6-membered); each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted $(C_1\text{-}C_{10})$ alkyl, $(C_1\text{-}C_{10})$ hydroxyalkyl, $(C_1\text{-}C_{10})$ alkyloxy-$(C_1\text{-}C_{10})$ alkyl, $(C_1\text{-}C_{10})$ alkylcarboxy-$(C_1\text{-}C_{10})$ alkyl, $(C_1\text{-}C_{10})$ alkylamino-$(C_1\text{-}C_{10})$ alkyl, $(C_1\text{-}C_{10})$ alkylamino-$(C_1\text{-}C_{10})$ alkylamino, $(C_1\text{-}C_{10})$ alkylamino-$(C_1\text{-}C_{10})$ alkylamino-$(C_1\text{-}C_{10})$ alkylamino, a substituted or unsubstituted $(C_1\text{-}C_{10})$ aminoalkyl, a substituted or unsubstituted aryl, a substituted or unsubstituted arylamino-$(C_1\text{-}C_{10})$ alkyl, $(C_1\text{-}C_{10})$ haloalkyl, $C_2\text{-}C_6$ alkenyl, $C_2\text{-}C_6$ alkynyl, oxo, a linking group attached to a second steroid, a substituted or unsubstituted $(C_1\text{-}C_{10})$ aminoalkyloxy, a substituted or unsubstituted $(C_1\text{-}C_{10})$ aminoalkyloxy-$(C_1\text{-}C_{10})$ alkyl, a substituted or unsubstituted $(C_1\text{-}C_{10})$ aminoalkylcarboxy, a substituted or unsubstituted $(C_1\text{-}C_{10})$ aminoalkylaminocarbonyl, a substituted or unsubstituted $(C_1\text{-}C_{10})$ aminoalkylcarboxamido, $H_2N$—HC$(Q_5)$-C(O)—O—, $H_2N$—HC$(Q_5)$-C(O)—N(H)—, $(C_1\text{-}C_{10})$ azidoalkyloxy, $(C_1\text{-}C_{10})$ cyanoalkyloxy, P.G.-HN—HC$(Q_5)$-C(O)—O—, $(C_1\text{-}C_{10})$ guanidinoalkyloxy, $(C_1\text{-}C_{10})$ quaternaryammoniumalkylcarboxy, and $(C_1\text{-}C_{10})$ guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ may be independently deleted when one of fused rings A, B, C, or D is unsaturated so as to complete the valency of the carbon atom at that site, or selected from the group consisting of hydrogen, hydroxyl, a substituted or unsubstituted $(C_1\text{-}C_{10})$ alkyl, $(C_1\text{-}C_{10})$ hydroxyalkyl, $(C_1\text{-}C_{10})$ alkyloxy-$(C_1\text{-}C_{10})$ alkyl, a substituted or unsubstituted $(C_1\text{-}C_{10})$ aminoalkyl, a substituted or unsubstituted aryl, $(C_1\text{-}C_{10})$ haloalkyl, $C_2\text{-}C_6$ alkenyl, $C_2\text{-}C_6$ alkynyl, oxo, a linking group attached to a second steroid, a substituted or unsubstituted $(C_1\text{-}C_{10})$ aminoalkyloxy, a substituted or unsubstituted $(C_1\text{-}C_{10})$ aminoalkylcarboxy, a substituted or unsubstituted $(C_1\text{-}C_{10})$ aminoalkylaminocarbonyl, $H_2N$—HC$(Q_5)$-C(O)—O—, $H_2N$—HC$(Q_5)$-C(O)—N(H)—, $(C_1\text{-}C_{10})$ azidoalkyloxy, $(C_1\text{-}C_{10})$ cyanoalkyloxy, P.G.-HN—HC$(Q_5)$-C(O)—O—, $(C_1\text{-}C_{10})$ guanidinoalkyloxy, and $(C_1\text{-}C_{10})$ guanidinoalkylcarboxy, where $Q_5$ is a side chain of any amino acid, P.G. is an amino protecting group, provided that at least two or three of $R_{1\text{-}4}$, $R_6$, $R_7$, $R_{11}$, $R_{12}$, $R_{15}$, $R_{16}$, $R_{17}$, and $R_{18}$ are independently selected from the group consisting of a substituted or unsubstituted $(C_1\text{-}C_{10})$ aminoalkyl, a substituted or unsubstituted $(C_1\text{-}C_{10})$ aminoalkyloxy, $(C_1\text{-}C_{10})$ alkylcarboxy-$(C_1\text{-}C_{10})$ alkyl, $(C_1\text{-}C_{10})$ alkylamino-$(C_1\text{-}C_{10})$ alkylamino, $(C_1\text{-}C_{10})$ alkylamino-$(C_1\text{-}C_{10})$ alkylamino-$(C_1\text{-}C_{10})$ alkylamino, a substituted or unsubstituted $(C_1\text{-}C_{10})$ aminoalkylcarboxy, a substituted or unsubstituted arylamino $(C_1\text{-}C_{10})$ alkyl, a substituted or unsubstituted $(C_1\text{-}C_{10})$ aminoalkyloxy-$(C_1\text{-}C_{10})$ aminoalkylaminocarbonyl, a substituted or unsubstituted $(C_1\text{-}C_{10})$ aminoalkylaminocarbonyl, a substituted or unsubstituted $(C_1\text{-}C_5)$ aminoalkylcarboxamido, a $(C_1\text{-}C_{10})$ quaternaryammonium alkylcarboxy, $H_2N$—HC$(Q_5)$-C(O)—O—, $H_2N$—HC$(Q_5)$-C(O)—N(H)—, $(C_1\text{-}C_{10})$ azidoalkyloxy, $(C_1\text{-}C_{10})$ cyanoalkyloxy, P.G.-HN—HC$(Q_5)$-C(O)—O—, $(C_1\text{-}C_{10})$ guanidinoalkyloxy, a $(C_1\text{-}C_{10})$ guanidinoalkylcarboxy, or a pharmaceutically acceptable salt thereof.

In Formula (II), at least two or three of $R_3$, $R_7$, or $R_{12}$ may independently include a cationic moiety attached to the Formula (II) structure via a hydrolysable linkage. Optionally, a tail moiety may be attached to Formula (II) at $R_{17}$. The tail moiety may be charged, uncharged, polar, nonpolar, hydrophobic, amphipathic, and the like. Although not required, at least two or three of m, n, p. and q are 1. In a preferred embodiment, m, n, and p=1 and q=0. Examples of such structures are shown in FIGS. 1A-1B.

In some embodiments, ceragenin compounds can be represented by Formula (III):

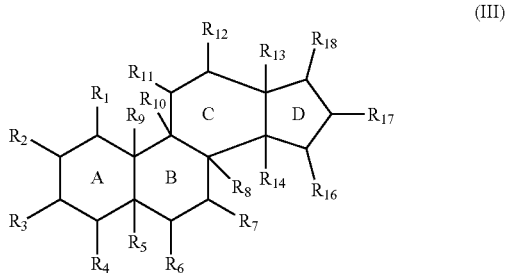

(III)

In some embodiments, rings A, B, C, and D are independently saturated.

In some embodiments, one or more of rings A, B, C, and D are heterocyclic.

In some embodiments, rings A, B, C, and D are non-heterocyclic.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternaryammoniumalkylcarboxy, and unsubstituted ($C_1$-$C_{18}$) guanidinoalkyl carboxy; and $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted aminoalkylcarboxy, an unsubstituted ($C_1$-$C_5$) ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternaryammoniumalkylcarboxy, and unsubstituted ($C_1$-$C_{16}$) guanidinoalkylcarboxy;

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; and alkylcarboxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_3$, $R_7$, and $R_{12}$ are aminoalkylcarboxy.

In some embodiments, $R_{18}$ is alkylaminoalkyl.
In some embodiments, $R_{18}$ is alkoxycarbonylalkyl.
In some embodiments, $R_{18}$ is di(alkyl)aminoalkyl.
In some embodiments, $R_{18}$ is alkylcarboxyalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, m, n, and p are each 1 and q is 0.

In some embodiments, ceragenin compounds can be represented by Formula (IV):

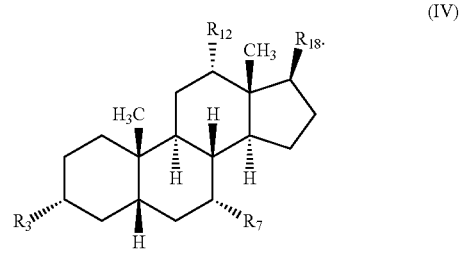

(IV)

In some embodiments, the CSA, or a pharmaceutically acceptable salt thereof, is:

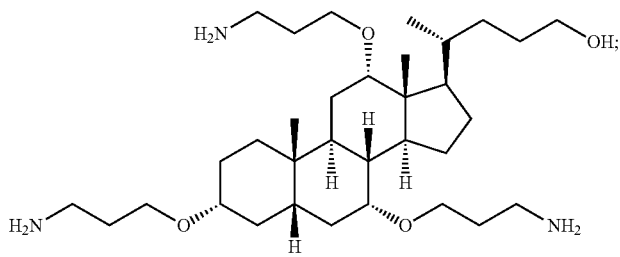

-continued
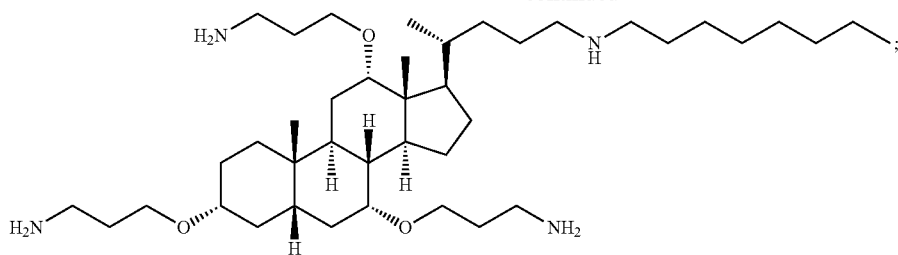
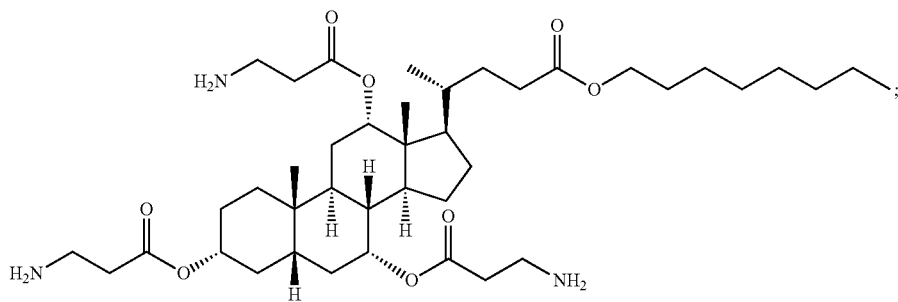
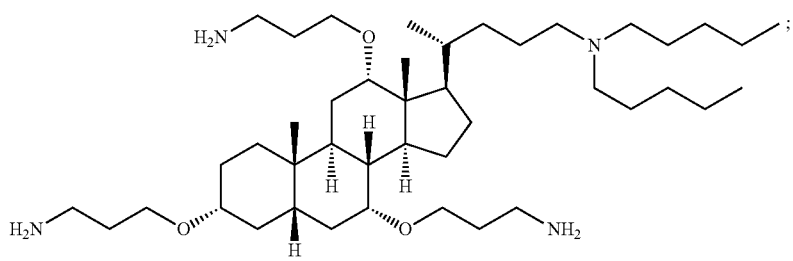
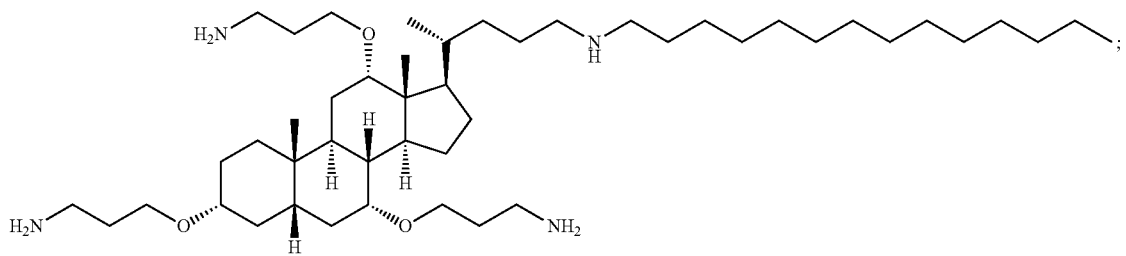
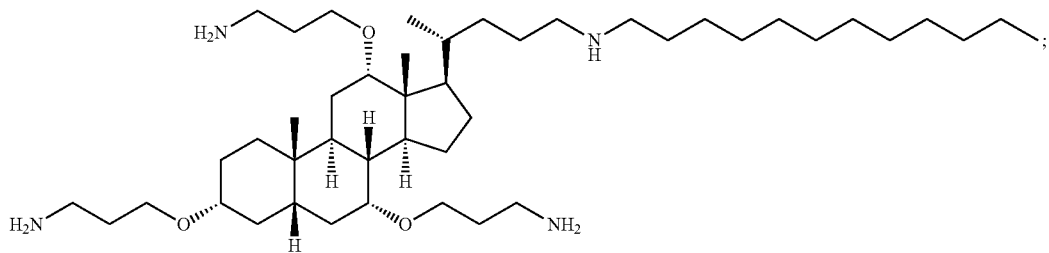
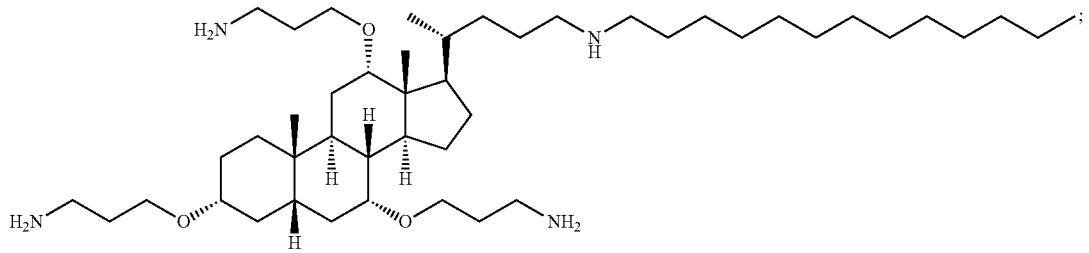

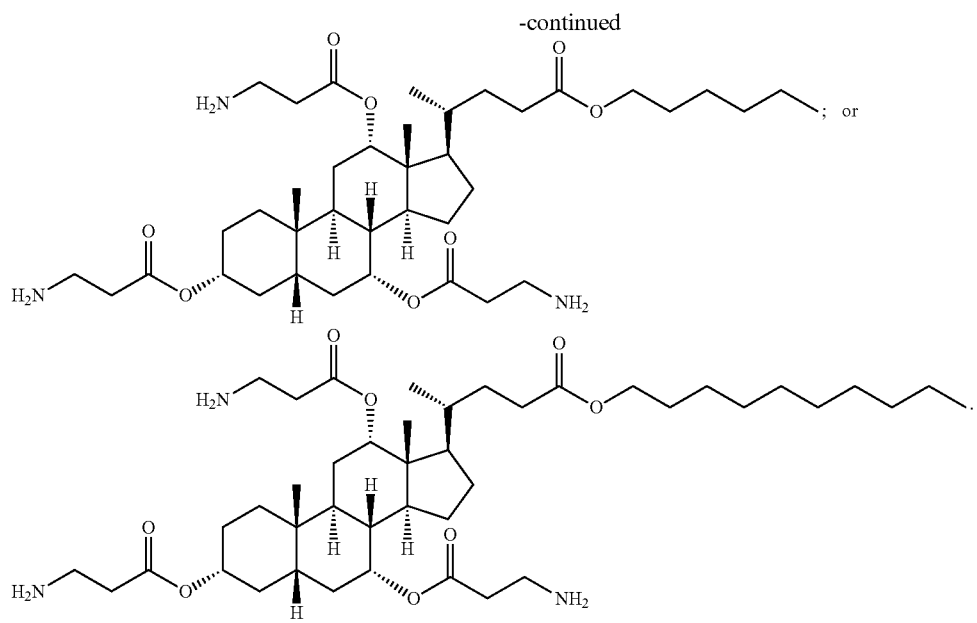
In some embodiments, the ceragenin compound is
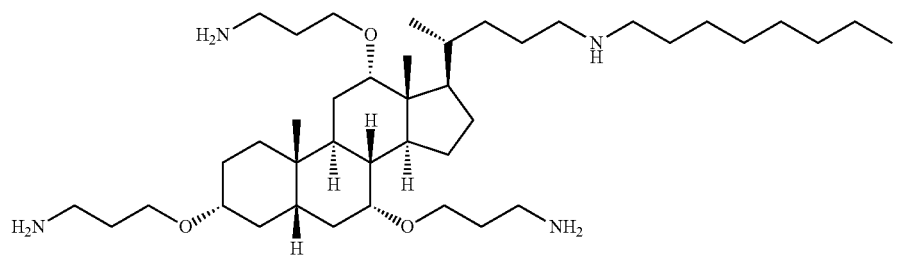
In other embodiments, the ceragenin compound is
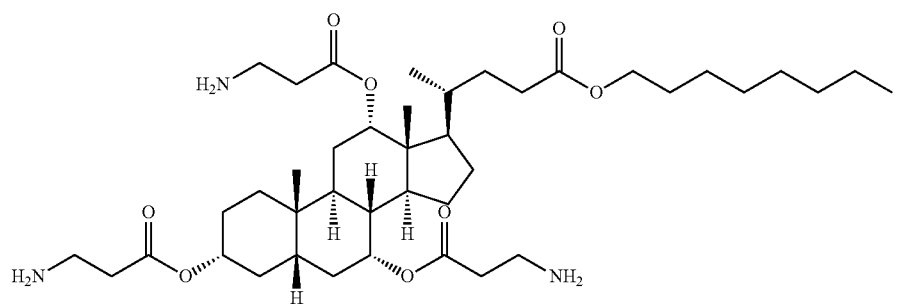
In other embodiments, the ceragenin compound is
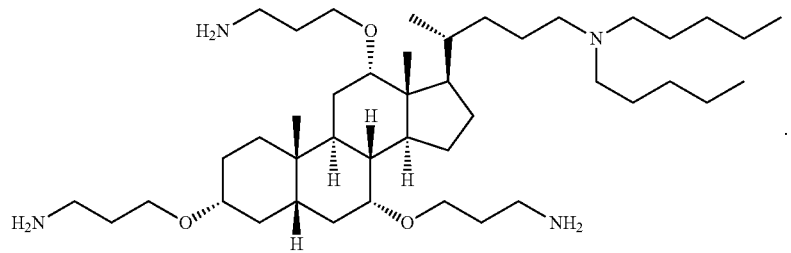

In other embodiments, the ceragenin compound is

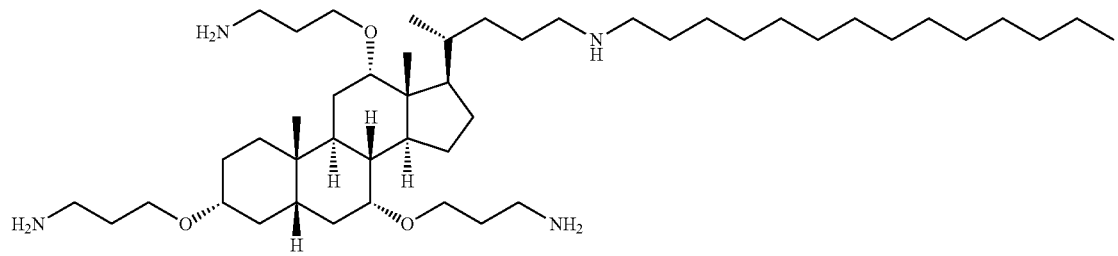

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, any "R" group(s) such as, without limitation, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ represent substituents that can be attached to the indicated atom. Unless otherwise specified, an R group may be substituted or unsubstituted.

The term "ring" as used herein can be heterocyclic or carbocyclic. The term "saturated" used herein refers to the fused ring of Formula (II) having each atom in the fused ring either hydrogenated or substituted such that the valency of each atom is filled. The term "unsaturated" used herein refers to the fused ring of Formula (II) where the valency of each atom of the fused ring may not be filled with hydrogen or other substituents. For example, adjacent carbon atoms in the fused ring can be doubly bound to each other. Unsaturation can also include deleting at least one of the following pairs and completing the valence of the ring carbon atoms at these deleted positions with a double bond; such as $R_5$ and $R_9$; $R_8$ and $R_{10}$; and $R_{13}$ and $R_{14}$.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, $R^aO(CH_2)_mO$—, $R^b(CH_2)_nO$—, $R^cC(O)O(CH_2)_pO$—, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms "alkyl" and "alkoxy" defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —$NH_2$ group.

As used herein, the term "hydroxy" refers to a —OH group.

A "cyano" group refers to a "—CN" group.

A "carbonyl" or an "oxo" group refers to a C=O group.

The term "azido" as used herein refers to a —N3 group.

As used herein, "aminoalkyl" refers to an amino group connected, as a substituent, via a lower alkylene group. Examples include $H_2N$-alkyl- with the term "alkyl" defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term "alkyl" as defined herein.

As used herein, "alkylaminoalkyl" refers to an alkyl group connected, as a substituent, to an amino group that is connected, as a substituent, to an alkyl group. Examples include alkyl-NH-alkyl-, with the term "alkyl" as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

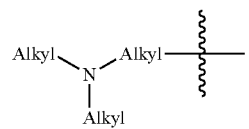

with the term "alkyl" as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term "alkyl" as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term "alkyl" as defined herein.

As used herein, "arylaminoalkyl" refers to an aryl group connected, as a substituent, to an amino group that is connected, as a substituent, to an alkyl group. Examples include aryl-NH-alkyl-, with the terms "aryl" and "alkyl" as defined herein.

As used herein, "aminoalkyloxy" refers to an amino group connected, as a substituent, to an alkyloxy group. Examples include H$_2$N-alkyl-O— and H$_2$N-alkoxy- with the terms "alkyl" and "alkoxy" as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms "alkyl" and "alkoxy" as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term "alkyl" as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term "alkyl" as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term "alkyl" as defined herein.

As used herein, "azidoalkyloxy" refers to an azido group connected as a substituent, to an alkyloxy group. Examples include N$_3$-alkyl-O— and N$_3$-alkoxy- with the terms "alkyl" and "alkoxy" as defined herein.

As used herein, "cyanoalkyloxy" refers to a cyano group connected as a substituent, to an alkyloxy group. Examples include NC-alkyl-O— and NC-alkoxy- with the terms alkyl and alkoxy as defined herein.

As used herein, "guanidinoalkyloxy" refers to a guanidinyl group connected, as a substituent, to an alkyloxy group. Examples include

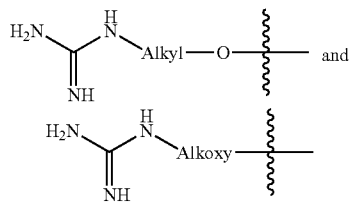

with the terms "alkyl" and "alkoxy" as defined herein.

As used herein, "guanidinoalkylcarboxy" refers to a guanidinyl group connected, as a substituent, to an alkyl group connected, as a substituent, to a carboxy group. Examples include

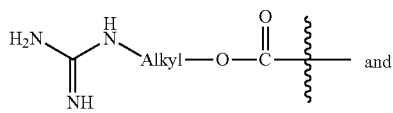

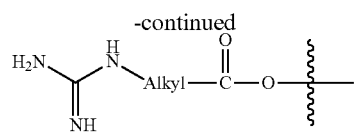

with the term "alkyl" as defined herein.

As used herein, "quaternaryammoniumalkylcarboxy" refers to a quaternized amino group connected, as a substituent, to an alkyl group connected, as a substituent, to a carboxy group. Examples include

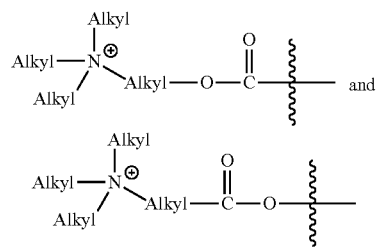

with the term "alkyl" as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is (C$_1$-C$_{10}$) alkyloxy-(C$_1$-C$_{10}$) alkyl.

The terms "P.G." or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

Ceragenin compounds include, but are not limited to, compounds having cationic groups (e.g., amine or guanidine groups) covalently attached to a steroid backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from any one or more of positions $R_3$, $R_7$, and $R_{12}$ of the sterol backbone.

Anti-microbial CSA compounds described herein may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$ of Formula (II). A tail moiety may include the heteroatom (O or N) covalently coupled to the sterol backbone.

The tail moiety may, for example, be configured to alter the hydrophobicity/hydrophilicity of the ceragenin compound. Ceragenin compounds of the present disclosure having different degrees of hydrophobicity/hydrophilicity may, for example, have different rates of uptake into different target microbes. Likewise, altering the hydrophobicity/hydrophilicity of the ceragenin compounds described herein may affect the retention of the ceragenin compounds in certain media.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

As used in this specification and the appended claims, the singular forms "a", "an", and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for delivering a ceragenin to a space, comprising:
    dispersing an aerosol of ceragenin particles or droplets consisting essentially of a ceragenin compound and a dispersant or filler into air of a space defined by one or more surfaces of a building, residential space, hospital, room, bathroom, kitchen, food preparation area, food packaging facility, restaurant, factory, laboratory, conduit, air duct, or ventilation system of a building and that includes one or more microbes, the ceragenin particles or droplets being less than 100 µm in size, wherein the ceragenin compound has a sterol backbone and a number of cationic groups attached thereto via covalent linkages; and
    the aerosol being suspended within the air of the space for a time period of at least 30 seconds and contacting one or more microbes within the space with the ceragenin compound.

2. The method of claim 1, further comprising dispersing the aerosol substantially evenly in the space such that the ceragenin compound can contact a number of spaced apart microbe-exposed surfaces in the space.

3. The method of claim 1, wherein the aerosol of ceragenin particles or droplets consists essentially of the ceragenin compound and a dispersant selected from the group consisting of water, alcohols, organic solvents, aqueous/organic emulsions, and combinations thereof.

4. The method of claim 3, wherein the ceragenin compound is dissolved in the dispersant.

5. The method of claim 3, wherein the dispersant includes a surfactant selected from the group consisting anionic surfactants, cationic surfactants, zwitterionic surfactants, nonionic surfactants, and combinations thereof.

6. The method of claim 1, wherein the ceragenin compound is capable of killing one or more microbes in the space in which it is dispersed.

7. The method of claim 1, wherein the ceragenin compound in the aerosol kills airborne microbes in the space.

8. The method of claim 1, wherein the ceragenin particles or droplets comprise liquid droplets having the ceragenin compound dispersed therein and a size in a range from about 0.1 µm to about 50 µm.

9. The method of claim 1, wherein the space is or is in at least one of a residence, a hospital, a food preparation facility, a food packaging facility, or a ventilation system.

10. The method of claim 1, wherein the space in which the ceragenin compound is dispersed includes one or more surfaces selected from the group consisting of metallic surfaces, ceramic surfaces, wooden surfaces, polymer surfaces, biological surfaces, and combinations thereof.

11. The method of claim 1, the method further comprising:
    allowing the ceragenin compound to degrade over a period of time after contacting the one or more surfaces of the space,
    wherein the ceragenin compound has a half-life of less than 40 days after contacting the one or more surfaces of the space.

12. The method of claim 1, wherein the ceragenin compound is capable of continuing to kill microbes on one or more microbe-exposed surfaces in of the space for at least one day after being deposited.

13. The method of claim 1, wherein the ceragenin compound is selected from the group consisting of CSA-1, CSA-26, CSA-38, CSA-40, CSA-46, CSA-48, CSA-53, CSA-55, CSA-57, CSA-60, CSA-90, CSA-107, CSA-109, CSA-110, CSA-112, CSA-113, CSA-118, CSA-124, CSA-130, CSA-139, CSA-141, CSA-142, CSA-32, CSA-35, CSA-41, CSA-45, CSA-47, CSA-49, CSA-52, CSA-56, and combinations thereof.

14. The method of claim 1, the aerosol being produced or dispersed by an area fogger, a smoke generating apparatus, an ultrasonic vaporizing apparatus, a jet nebulizer, an ultrasonic nebulizer, or a vibrating disc nebulizer.

15. The method of claim 1, the aerosol being produced or dispersed by:
   a nebulizer having a liquid reservoir and an outlet nozzle capable of delivering an aerosol; and
   a ceragenin composition contained in the liquid reservoir comprising:
      a dispersant; and
      the ceragenin compound suspended in the dispersant.

16. The method of claim 15, wherein the dispersant comprises a sterile, isotonic saline solution and, optionally, at least one surfactant.

17. The method of claim 1, wherein the aerosol of ceragenin particles or droplets consists essentially of the ceragenin compound and a filler selected from the group consisting of cellulose, dibasic calcium phosphate, lactose, sucrose, glucose, mannitol, sorbitol, calcium carbonate, magnesium stearate, tricalcium phosphate, sodium bicarbonate, sodium ferrocyanide, potassium ferrocyanide, calcium ferrocyanide, sodium silicate, silicon dioxide, calcium silicate, magnesium trisilicate, talc, sodium aluminosilicate, potassium aluminium silicate, calcium aluminosilicate, bentonite, aluminium silicate, stearic acid, and combinations thereof.

18. A method for delivering a ceragenin to a space, comprising:
   providing an aerosol container having a dispensing member capable of delivering the aerosol, wherein the aerosol container contains a ceragenin composition that includes:
      a dispersant;
      a ceragenin compound suspended or dissolved in the dispersant, the ceragenin compound having a sterol backbone and a number of cationic groups attached thereto; and
      a propellant;
   dispersing an aerosol of the ceragenin composition from the aerosol container into air of a space, wherein the aerosol includes liquid droplets and/or solid particles having a size in a range from about 0.1 μm to about 50 μm; and
   the aerosol being suspended within the air of the space for a time period of at least 1 minute and the ceragenin compound killing one or more microbes in the space.

19. The method of claim 18, the ceragenin compound killing one or more microbes in the space that are airborne.

20. The method of claim 18, the aerosol being suspended within the air of the space for a time period of at least 5 minutes.

21. The method of claim 18, the aerosol being suspended within the air of the space for a time period of at least 15 minutes.

22. The method of claim 18, the aerosol being suspended within the air of the space for a time period of at least 30 minutes.

23. The method of claim 18, the aerosol being suspended within the air of the space for a time period of at least 1 hour.

24. A method for delivering a ceragenin to a space, comprising:
   dispersing an aerosol consisting essentially of a ceragenin compound and a dispersant or filler into air of a space defined or enclosed by one or more surfaces selected from the group consisting of metallic surfaces, ceramic surfaces, wooden surfaces, polymer surfaces, and combinations thereof; and
   the aerosol being suspended within the air of the space for a time period of at least 30 seconds and contacting one or more microbes within the space with the ceragenin compound.

25. The method of claim 24, wherein the one or more surfaces include at least one of a bathroom surface, a kitchen surface, a food preparation surface, a food packaging surface, a hospital surface, a baseboard surface, a wall surface, a conduit surface, an air duct surface, an air handling surface, or a laboratory surface.

26. The method of claim 24, the aerosol being suspended within the air of the space for a time period of at least 5 minutes.

* * * * *

UNITED STATES PATENT AND TRADEMARK OFFICE
CERTIFICATE OF CORRECTION

| | | |
|---|---|---|
| PATENT NO. | : 9,533,063 B1 | Page 1 of 1 |
| APPLICATION NO. | : 13/783007 | |
| DATED | : January 3, 2017 | |
| INVENTOR(S) | : Savage | |

It is certified that error appears in the above-identified patent and that said Letters Patent is hereby corrected as shown below:

In the Specification

Column 3
Lines 1-2, change "appended drawing." to --appended drawings.--
Line 2, change "that this drawing depicts only" to --that these drawings depict only--
Line 3, change "and is therefore" to --and are therefore--
Line 6, change "drawing" to --drawings--

Column 8
Lines 28-29, change "ultrasonic foggers, pressurized canisters, ultrasonic foggers, nebulizers" to
--ultrasonic foggers, pressurized canisters, nebulizers--

Column 9
Line 61, change "and ban be" to --and can be--

Column 10
Line 52, change "a space is includes" to --a space includes--

Column 26
Line 39, change "2 carbon atom" to --2 carbon atoms--
Line 55, change "2 carbon atom" to --2 carbon atoms--

Column 27
Line 16, change "6 carbon atom" to --6 carbon atoms--

In the Claims

Column 32
Line 36, change "consisting anionic" to --consisting of anionic--
Line 66, change "surfaces in of the space" to --surfaces of the space--

Signed and Sealed this
Fourth Day of April, 2017

Michelle K. Lee
*Director of the United States Patent and Trademark Office*